US012285497B2

(12) United States Patent
Rodino-Klapac et al.

(10) Patent No.: US 12,285,497 B2
(45) Date of Patent: Apr. 29, 2025

(54) SELF-COMPLEMENTARY ADENO-ASSOCIATED VIRUS VECTOR AND ITS USE IN TREATMENT OF MUSCULAR DYSTROPHY

(71) Applicant: RESEARCH INSTITUTE AT NATIONWIDE CHILDREN'S HOSPITAL, Columbus, OH (US)

(72) Inventors: Louise Rodino-Klapac, Columbus, OH (US); Jerry R. Mendell, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 18/046,740

(22) Filed: Oct. 14, 2022

(65) Prior Publication Data

US 2023/0139985 A1    May 4, 2023

Related U.S. Application Data

(60) Provisional application No. 63/256,368, filed on Oct. 15, 2021.

(51) Int. Cl.
*A61K 48/00* (2006.01)
*A61K 38/17* (2006.01)
(Continued)

(52) U.S. Cl.
CPC ...... *A61K 48/0066* (2013.01); *A61K 38/1719* (2013.01); *A61P 21/00* (2018.01);
(Continued)

(58) Field of Classification Search
CPC . A61K 48/0066; A61K 38/1719; A61P 21/00; C12N 15/86; C12N 2750/14143; C12N 2750/14145; C12N 2830/15
See application file for complete search history.

(56) References Cited

U.S. PATENT DOCUMENTS

| 5,173,414 A | 12/1992 | Lebkowski et al. |
| 5,449,616 A | 9/1995 | Campbell et al. |

(Continued)

FOREIGN PATENT DOCUMENTS

| CN | 101896186 A | 11/2010 |
| EP | 0 127 839 A2 | 12/1984 |

(Continued)

OTHER PUBLICATIONS

Raj et al., "Self-complementary adeno-associated viral vectors for gene therapy of hemophilia B: progress and challenges" Expert Rev Hematol. (2011) 4(5): 539-549 (Year: 2011).*

(Continued)

*Primary Examiner* — Evelyn Y Pyla
*Assistant Examiner* — Katherine R Small
(74) *Attorney, Agent, or Firm* — Foley & Lardner LLP

(57) ABSTRACT

Described herein are methods of treating muscular dystrophy comprising administering a self complementary recombinant AAV (rAAV) ScAAVrh74.MIHCK7.h8GCB vector, methods of expressing beta-sarcoglycan gene in a patient, pharmaceutical compositions comprising the rAAV, and methods of generating the rAAV.

11 Claims, 10 Drawing Sheets

Specification includes a Sequence Listing.

(51) Int. Cl.
*A61P 21/00* (2006.01)
*C12N 15/86* (2006.01)

(52) U.S. Cl.
CPC .... *C12N 15/86* (2013.01); *C12N 2750/14143* (2013.01); *C12N 2750/14145* (2013.01); *C12N 2830/15* (2013.01)

(56) References Cited

U.S. PATENT DOCUMENTS

| | | |
|---|---|---|
| 5,658,776 A | 8/1997 | Flotte et al. |
| 5,672,694 A | 9/1997 | Campbell et al. |
| 5,786,211 A | 7/1998 | Johnson |
| 5,871,982 A | 2/1999 | Wilson et al. |
| 6,204,059 B1 | 3/2001 | Samulski et al. |
| 6,258,595 B1 | 7/2001 | Gao et al. |
| 6,262,035 B1 | 7/2001 | Campbell et al. |
| 6,566,118 B1 | 5/2003 | Atkinson et al. |
| 6,632,800 B1 | 10/2003 | Russell et al. |
| 7,282,199 B2 | 10/2007 | Gao et al. |
| 7,790,449 B2 | 9/2010 | Gao et al. |
| 7,883,858 B2 | 2/2011 | Hood et al. |
| 9,061,059 B2 | 6/2015 | Chakraborty et al. |
| 9,434,928 B2 | 9/2016 | Mendell et al. |
| 10,105,453 B2 | 10/2018 | Mendell et al. |
| 11,358,993 B2 | 6/2022 | Rodino-Klapac et al. |
| 2001/0029040 A1 | 10/2001 | Toyo-Oka |
| 2003/0225260 A1 | 12/2003 | Snyder |
| 2006/0154250 A1 | 7/2006 | Morris et al. |
| 2007/0099251 A1 | 5/2007 | Zhang et al. |
| 2008/0249052 A1 | 10/2008 | Duan et al. |
| 2009/0054823 A1 | 2/2009 | Bridges et al. |
| 2009/0275107 A1 | 11/2009 | Lock et al. |
| 2009/0280103 A1 | 11/2009 | Flueck |
| 2010/0003218 A1 | 1/2010 | Duan et al. |
| 2010/0008979 A1 | 1/2010 | Tomatsu et al. |
| 2010/0026655 A1 | 2/2010 | Harley |
| 2010/0075866 A1 | 3/2010 | Hood et al. |
| 2010/0112694 A1 | 5/2010 | Marban |
| 2010/0120627 A1 | 5/2010 | Belouchi et al. |
| 2010/0247495 A1 | 9/2010 | Ichim et al. |
| 2010/0266551 A1 | 10/2010 | Richard et al. |
| 2011/0023139 A1 | 1/2011 | Weinstein et al. |
| 2011/0053221 A1 | 3/2011 | Chen et al. |
| 2011/0070210 A1 | 3/2011 | Andrijauskas |
| 2011/0076744 A1 | 3/2011 | Wright et al. |
| 2011/0082192 A1 | 4/2011 | Milne et al. |
| 2011/0104120 A1 | 5/2011 | Xiao et al. |
| 2011/0266551 A1 | 11/2011 | Thompson et al. |
| 2011/0294193 A1 | 12/2011 | Amalfitano et al. |
| 2011/0301226 A1 | 12/2011 | Mendell et al. |
| 2012/0087862 A1 | 4/2012 | Hood et al. |
| 2013/0171172 A1 | 7/2013 | Richard et al. |
| 2014/0010861 A1 | 1/2014 | Bancel et al. |
| 2014/0147432 A1 | 5/2014 | Chakraborty et al. |
| 2014/0179770 A1 | 6/2014 | Zhang et al. |
| 2014/0234255 A1 | 8/2014 | Lai et al. |
| 2014/0249208 A1 | 9/2014 | Chakraborty et al. |
| 2014/0256802 A1 | 9/2014 | Boye et al. |
| 2014/0273231 A1 | 9/2014 | Zhang et al. |
| 2014/0323956 A1 | 10/2014 | Mendell et al. |
| 2015/0111955 A1 | 4/2015 | High et al. |
| 2015/0125429 A1 | 5/2015 | Perlingeiro et al. |
| 2015/0232883 A1 | 8/2015 | Dahlman et al. |
| 2015/0238627 A1 | 8/2015 | Leger et al. |
| 2016/0058890 A1 | 3/2016 | Buj Bello et al. |
| 2018/0256752 A1 | 9/2018 | Buj Bello et al. |
| 2019/0000998 A1 | 1/2019 | Mendell et al. |
| 2019/0202880 A1 | 7/2019 | Rodino-Klapac et al. |
| 2019/0343966 A1 | 11/2019 | Wang et al. |
| 2020/0339960 A1 | 10/2020 | Sahenk |
| 2021/0128749 A1 | 5/2021 | Rodino-Klapac et al. |
| 2021/0393801 A1 | 12/2021 | Rodino-Klapac et al. |
| 2023/0390417 A1 | 12/2023 | Sahenk |

FOREIGN PATENT DOCUMENTS

| | | |
|---|---|---|
| EP | 0 155 476 A | 9/1985 |
| EP | 2 859 896 A1 | 4/2015 |
| EP | 3 030 666 A | 6/2016 |
| JP | 2015-509711 A | 4/2015 |
| WO | 95/03392 A1 | 2/1995 |
| WO | 95/13365 A1 | 5/1995 |
| WO | 95/13392 A1 | 5/1995 |
| WO | 96/17947 A1 | 6/1996 |
| WO | 97/06243 A1 | 2/1997 |
| WO | 97/08298 A1 | 3/1997 |
| WO | 97/09441 A2 | 3/1997 |
| WO | 97/21825 A1 | 6/1997 |
| WO | 98/09657 A2 | 3/1998 |
| WO | 99/01176 A1 | 1/1999 |
| WO | 99/11764 A2 | 3/1999 |
| WO | WO-99/43360 A1 | 9/1999 |
| WO | 01/83692 A2 | 11/2001 |
| WO | 02/53703 A2 | 7/2002 |
| WO | WO-03/074714 A1 | 9/2003 |
| WO | 2004/058146 A2 | 7/2004 |
| WO | WO-2007/057781 A2 | 5/2007 |
| WO | WO-2009/019505 A2 | 2/2009 |
| WO | 2009/054725 A2 | 4/2009 |
| WO | 2013/016352 A1 | 1/2013 |
| WO | 2013/078316 A1 | 5/2013 |
| WO | 2013/123503 A1 | 8/2013 |
| WO | 2013/151665 A2 | 10/2013 |
| WO | WO-2013/176772 A1 | 11/2013 |
| WO | WO-2014/037526 A1 | 3/2014 |
| WO | WO-2014/039916 A1 | 3/2014 |
| WO | WO-2014/093622 A2 | 6/2014 |
| WO | WO-2014/093712 A1 | 6/2014 |
| WO | WO-2014/204725 A1 | 12/2014 |
| WO | WO-2015/018503 A1 | 2/2015 |
| WO | WO-2015/021457 A2 | 2/2015 |
| WO | 2015/110449 A1 | 7/2015 |
| WO | WO-2015/158749 A2 | 10/2015 |
| WO | 2015/197232 A1 | 12/2015 |
| WO | WO-2016/115543 A2 | 7/2016 |
| WO | WO-2017/087395 A1 | 5/2017 |
| WO | WO-2017/165859 A1 | 9/2017 |
| WO | 2017/180857 A1 | 10/2017 |
| WO | WO-2017/181014 A1 | 10/2017 |
| WO | WO-2017/181015 A1 | 10/2017 |
| WO | WO-2017180976 A1 * | 10/2017 ......... A61K 48/0058 |
| WO | WO-2017/221145 A1 | 12/2017 |
| WO | WO-2018/170408 A1 | 9/2018 |
| WO | WO-2019/012336 A2 | 1/2019 |
| WO | WO-2019/078916 A1 | 4/2019 |
| WO | WO-2019/118806 A1 | 6/2019 |
| WO | 2019/152474 A1 | 8/2019 |
| WO | WO-2019/195362 A1 | 10/2019 |
| WO | WO-2019/209777 A1 | 10/2019 |
| WO | WO-2019/245973 A1 | 12/2019 |
| WO | WO-2020/006458 A1 | 1/2020 |
| WO | WO-2020/123645 A1 | 6/2020 |
| WO | WO-2020/176614 A1 | 9/2020 |
| WO | WO-2021/035120 A1 | 2/2021 |
| WO | 2021/257655 A1 | 12/2021 |

OTHER PUBLICATIONS

Anderson et al., Nucleic Acid Hybridisation: A Practical Approach, IRL Press Limited, Oxford, England, Ch. 4.

Angelini et al., The clinical spectrum of sarcoglycanopathies. Neurology. 52:176-179 (1999).

Araishi et al., Loss of the sarcoglycan complex and sarcospan leads to muscular dystrophy in beta-sarcoglycan-deficient mice, Hum. Mol. Genet., 8(9):1589-1598 (1999).

Barresi et al., Disruption of heart sarcoglycan complex and severe cardiomyopathy caused by beta sarcoglycan mutations, J. Med. Genet., 37(2):102-107 (2000).

Beastrom et al., mdx(5cv) mice manifest more severe muscle dysfunction and diaphragm force deficits than do mdx Mice, Am. J. Pathol., 179(5):2464-74 (2011).

(56) References Cited

OTHER PUBLICATIONS

Bonnemann et al., Betasarcoglycan (A3b) mutations cause autosomal recessive muscular dystrophy with loss of the sarcoglycan complex, Nat. Genet., 11(3):266-273 (1995).
Bonnemann et al., Genomic screening for beta-sarcoglycan gene mutations: missense mutations may cause severe limb-girdle muscular dystrophy type 2E (LGMD 2E), Hum. Mol. Genet., 5(12):1953-1961 (1996).
Carter, Adeno-associated virus vectors, Current Opinions in Biotechnology, 3(5):533-539 (1992).
Chao et al., Several log increase in therapeutic transgene delivery by distinct adeno-associated viral serotype vectors, Mol. Ther., 2(6):619-623 (2000).
Chao et al., Sustained and complete phenotype correction of hemophilia B mice following intramuscular injection of AAV1 serotype vectors, Mol. Ther., 4(3):217-222 (2001).
Chicoine et al., Plasmapheresis eliminates the negative impact of AAV antibodies on microdystrophin gene expression following vascular delivery, Mol. Ther., 22(2):338-347 (2014).
Chicoine et al., Vascular delivery of rAAVrh74.MCK.GALGT2 to the gastrocnemius muscle of the rhesus macaque stimulates the expression of dystrophin and laminin a2 surrogates. Mol. Ther. 22:713-724 (2014).
Chu et al., SV40 DNA transfection of cells in suspension: analysis of efficiency of transcription and translation of T-antigen, Gene., 13(2):197-202 (1981).
Clark et al., Highly purified recombinant adeno-associated virus vectors are biologically active and free of detectable helper and wild-type viruses, Hum. Gene. Ther., 10(6):1031-1039 (1999).
Clark et al., Recombinant adeno-associated viral vectors mediate long-term transgene expression in muscle, Hum. Gene. Ther., 8(6):659-669 (1997).
Clark et at., A stable cell line carrying adenovirus—inducible rep and cap genes allows for infectivity titration of adeno-associated virus vectors, Gene. Ther. 3:1124-32 (1996).
Cserjesi et al., Myogenin induces the myocyte-specific enhancer binding factor MEF-2 independently of other muscle-specific gene products, Mol. Cell. Biol., 11(10):4854-4862 (1991).
De et al., High levels of persistent expression of alpha1-antitrypsin mediated by the nonhuman primate serotype rh.10 adeno-associated virus despite preexisting immunity to common human adeno-associated viruses, Mol. Ther. 13:67-76 (2006).
Draviam et al., The—li-core of sarcoglycan is essential for deposition at the plasma membrane, Muscle and Nerve. 34:691-701 (2006).
Dressman et al., Delivery of alpha- and beta-sarcoglycan by recombinant adeno-associated virus: efficient rescue of muscle, but differential toxicity, Hum. Gene. Ther., 13(13):1631-1646 (2002).
Dressman, D., AAV-Mediated gene transfer to models of muscular dystrophy: Insights into assembly of multi-subunit membrane proteins, University of Pittsburgh (1997).
Durbeej et al., Disruption of the beta-sarcoglycan gene reveals pathogenetic complexity of limb-girdle muscular dystrophy type 2E, Mol. Cell., 5(1):141-151 (2000).
European Application No. 22201580.2, European Search Report and Opinion, mailed Jul. 4, 2023.
Fanin et al., LGMD2E patients risk developing dilated cardiomyopathy, Neuromuscl. Disord., 13(4):303-309 (2003).
Flotte et al., Gene expression from adeno-associated virus vectors in airway epithelial cells, Am. J. Respir Mol. Biol. 7:349-356. 1992.
Fowler, et al., Improved knockdown from artificial microRNAs in an enhanced miR-155 Backbone: a designer's guide to potent multi-target RNAi, Nucleic Acids Research, 44(5): e48, (Nov. 2015).
Francois et al., Accurate titration of infectious AAV particles requires measurement of biologically active vector genomes and suitable controls, Mol. Ther., 10:223-236, (Sep. 2018).
Gao et al., Clades of Adeno-associated Viruses Are Widely Disseminated in Human Tissues, J. Virol., 78:6381-6388 (2004).

GenBank Accession No. AF085716.1, Adena-associated virus 5 DNA binding trs helicase (Rep22) and capsid protein (VP1) aenes, complete eds, Feb. 9, 1999.
GenBank Accession No. AX753246.1, Sequence 1 from Patent EP1310571, Jun. 23, 2003.
GenBank Accession No. AX753249.1, Sequence 4 from Patent EP1310571, Jun. 23, 2003.
Genbank Accession No. NC_001401.0, Adena-associated virus—2, complete genome, Aug. 13, 2018.
Genbank Accession No. NC_001729.1, Adena-associated virus—3, complete genome, Aug. 13, 2018.
GenBank Accession No. NC_001829.1, Adena-associated virus—4, complete genome, Aug. 13, 2018.
GenBank Accession No. NC_001862, Adena-associated virus 6, complete genome, Jan. 12, 2004.
Genbank Accession No. NC_002077.1, Adena-associated virus—1, complete genome, Aug. 13, 2018.
Genbank Accession No. NM_00232.4, *Homo sapiens* sarcoglycan beta (SGCB), Mrna, Feb. 20, 2019.
Genbank Accession No. NP_000233.1, Beta Sarcoglyan (43kD dystrophin-associated glycoprotein) *Homo sapiens*, Mar. 19, 1999.
GenBank: Accession No. NP_000223.1: beta-sarcoglycan sequence, dated Mar. 3, 1999.
Georganopoulou et al., A Journey with LGMD: From Protein Abnormalities to Patient Impact, Protein J., 40(4):466-488 (2021).
Gibertini et al., Fibrosis and inflammation are greater in muscles of beta-sarcoglycan-null mouse than mdx mouse, Cell Tissue Res., 356(2):427-443 (2014).
Graham et al., A new technique for the assay of infectivity of human adenovirus 5 DNA, Virology, 52(2):456-67 (1973).
Greig et al., Impact of intravenous infusion time on AAV8 vector pharmacokinetics, safety, and liver transduction in cynomolgus macaques, Mol. Ther. Methods Clin. Dev., 3(C):16079 (2016).
Grieger et al., Production and characterization of adeno-associated viral vectors, Nat. Protoc., 1(3):1412-1428 (2006).
Griffin et al., Preclinical Systemic Delivery of Adeno-Associated a-Sarcoglycan Gene Transfer for Limb-Girdle Muscular Dystrophy, Hum. Gene Ther., 32(7-8):390-404 (2021).
Hakim et al., The passive mechanical properties of the extensor digitorum longus muscle are compromised in 2- to 20-mo-old mdx mice, J. Appl. Physiol., 110(6):1656-1663 (2011).
Hermonat et al., Use of adeno-associated virus as a mammalian DNA cloning vector: transduction of neomycin resistance into mammalian tissue culture cells, Proc. Natl. Acad. Sci. USA. 81:6466-70 (1984).
Herzog et al., Stable gene transfer and expression of human blood coagulation factor IX after intramuscular injection of recombinant adeno-associated virus, Proc. Natl. Acad. Sci. USA, 94(11):5804-5809 (1997).
Inouye et al., Codon optimization of genes for efficient protein expression in mammalian cells by selection of only preferred human codons, Protein Expression and Purification, 109: 47-54, (May 2015).
International Application No. PCT/US2017/027583, International Preliminary Report on Patentability, mailed Oct. 25, 2018.
Sambrook et al., Cold spring harbor laboratory press, Cold Spring Harbor, N.Y., (2001).
Sambrook et al., Molecular Cloning: A Laboratory Manual, Cold Spring Harbor Laboratory, Cold Spring Harbor, New York (2nd ed. 1989).
Samulski et al., Cloning of adeno-associated virus into pBR322: rescue of intact virus from the recombinant plasmid in human cells, Proc. Natl. Acad. Sci. USA. 79:2077-81 (1982).
Samulski et al., Helper-free stocks of recombinant adeno-associated viruses: normal integration does not require viral gene expression, J. Virol. 63:3822-8 (1989).
Sandona et al., Sarcoglycanopathies: molecular pathogenesis and therapeutic prospects, Exp Rev. Mol. Med. 11:e28 (2009).
Sarepta Therapeutics: Sarepta Therapeutics' Investigational Gene Therapy SRP-9003 for the Treatment of Limb-Girdle Muscular Dystrophy Type 2E Shows Sustained Expression and Functional Improvements 2 Years After Administration, 1-3 (2021).

(56) References Cited

OTHER PUBLICATIONS

Schnepp et al., Highly purified recombinant adeno-associated virus vectors. Preparation and quantitation, Methods Mol. Med. 69:427-43 (2002).
Semenza et al., Hypoxia-inducible nuclear factors bind to an enhancer element located 3' to the human erythropoietin gene, Proc. Natl. Acad. Sci. U.S.A., 88(13):5680-5684 (1991).
Semplicini et al., Clinical and genetic spectrum in limb-girdle muscular dystrophy type 2E, Neurology. 84:1772-81 (2015).
Senapathy et al., Molecular cloning of adeno-associated virus variant genomes and generation of infectious virus by recombination in mammalian cells, J. Biol. Chem., 259:4661-4666 (1984).
Shield et al., E-box sites and a proximal regulatory region of the muscle creatine kinase gene differentially regulate expression in diverse skeletal muscles and cardiac muscle of transgenic mice, Mol. Cell. Biol., 16(9):5058-5068 (1996).
Srivastava et al., Nucleotide sequence and organization of the adeno-associated virus 2 genome, J. Virol. 45:555-64 (1983).
Straub et al., Animal models for muscular dystrophy show different patterns of sarcolemmal disruption, J. Cell. Biol., 139(2):375-385 (1997).
Sun et al., Correction of Multiple Striated Muscles in Murine Pompe Disease Through Adena—Associated Virus-mediated Gene Therapy, Mol. Ther., 16(8):1366-71 (2008).
Sveen et al., Cardiac involvement in patients with limb-girdle muscular dystrophy type 2 and Becker muscular dystrophy, Arch. Neurol., 65(9):1196-1201 (2008).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated virus vector for high-frequency integration, expression, and rescue of genes in mammalian cells, Mol. Cell. Biol., 5(11):3251-3260 (1985).
Voikar et al., Long-term individual housing in C57BL/6J and DBA/2 mice: assessment of behavioral consequences, Genes Brain Behav., 4(4):240-52 (2005).
Wang et al., Construction and analysis of compact muscle-specific promoters for AAV vectors, Gene. Ther., 15(22):1489-1499 (2008).
Wang et al., Loss of miR-29 in myoblasts contributes to dystrophic muscle pathogenesis, Mol. Ther., 20(6):1222-33 (2012).
Wein et al., Translation from a DMD exon 5 IRES results in a functional dystrophin isoform that attenuates dystrophinopathy in humans and mice, Nat. Med., 20(9):992-1000 (2014).
Weintraub et al., The myoD gene family: nodal point during specification of the muscle cell lineage, Science. 251:761-766 (1991).
Wong-Kisiel et al., Two siblings with limb-girdle muscular dystrophy type 2E responsive to deflazacort, Neuromusc. Disord., 20(2):122-124 (2010).
Xiao et al., Efficient long-term gene transfer into muscle tissue of immunocompetent mice by adeno-associated virus vector, J. Virol., 70(11):8098-8108 (1996).
Xiao et al., Production of High-Titer Recombinant Adeno-Associated Virus Vectors in the Absence of Helper Adenovirus, J. Virol., 72:2224-2232 (1998).
Xu et al., An Isolated Limb Infusion Method Allows for Broad Distribution of rAAVrh74.MCK.GALGT2 to Leg Skeletal Muscles in the Rhesus Macaque, Mol. Ther. Methods Clin. Dev., 10:89-104 (2018).
Zanotti et al., Opposing roles of miR-21 and miR-29 in the progression of fibrosis in Duchenne muscular dystrophy., Biochem. Biophys. Acta., 1852:1451-4 (2015).
Zhang et al., Dual AAV therapy ameliorates exercise-induced muscle injury and functional ischemia in murine models of Duchenne muscular dystrophy, Hum. Mol. Genet. 22:3720-9 (2013).
International Application No. PCT/US2017/027583, International Search Report and Written Opinion, mailed Jul. 14, 2017.
International Application No. PCT/US2020/019892, International Preliminary Report on Patentability, mailed Sep. 10, 2021.
International Application No. PCT/US2020/019892, International Search Report and Written Opinion, mailed May 14, 2020.
International Preliminary Report on Patentability, PCT/US2017/027636 (Oct. 16, 2018).
International Search Report and Written Opinion, PCT/US2017/027636 (Jul. 5, 2017).
Johnson et al., Muscle creatine kinase sequence elements regulating skeletal and cardiac muscle expression in transgenic mice, Mol. Cell. Biol., 9(8):3393-3399 (1989).
Kessler et al., Gene delivery to skeletal muscle results in sustained expression and systemic delivery of a therapeutic protein, Proc. Nat. Acad. Sci. USA, 93(24):14082-14087 (1996).
Kobayashi et al., Sarcolemma-localized nNOS is required to maintain activity after mild exercise, Nature. 456:511-5 (2008).
Kotin et al., Manufacturing Clinical Grade Recombinant Adena-Associated Virus Using Invertebrate Cell Lines, Hum. Gene Ther., 28(4):350-360 (2017).
Laughlin et al., Cloning of infectious adeno-associated virus genomes in bacterial plasmids, Gene., 23(1):65-73 (1983).
Laws et al., Progression of kyphosis in mdx mice, J. Appl. Physiol. 97:1970-7 (2004).
Lebkowski et al., Adeno-associated virus: a vector system for efficient introduction and integration of DNA into a variety of mammalian cell types, Mol. Cell. Biol., 8(10: 3988-3996, (Oct. 1988).
Lewis et al., Generation of neutralizing activity against human immunodeficiency virus type 1 in serum by antibody gene transfer, J. Virol., 76(17):8769-8775 (2002).
Liu et al., Adeno-associated virus-mediated microdystrophin expression protects young mdx muscle from contraction-induced injury, Mol. Ther., 11(2):245-256 (2005).
Mader et al., A steroid-inducible promoter for the controlled overexpression of cloned genes in eukaryotic cells, Proc. Natl. Acad. Sci. U.S.A., 90(12):5603-5607 (1993).
Marsic et al., Vector design Tour de Force: integrating combinatorial and rational approaches to derive novel adeno-associated virus variants, Molecular Therapy, 22(11):1900-1909 (2014).
Matsuda et al., Visualization of dystrophic muscle fibers in mdx mouse by vital staining with Evans blue: evidence of apoptosis in dystrophin-deficient muscle, J. Biochem., 118(5):959-964 (1995).
McCarty et al., Adeno-associated virus terminal repeat (TR) mutant generates self-complementary vectors to overcome the rate-limiting step to transduction in vivo, Gene. Ther., 10(26):2112-2118 (2003).
McCarty et al., Self-complementary recombinant adeno-associated virus (scAAV) vectors promote efficient transduction independently of DNA synthesis, Gene. Ther., 8(16):1248-1254 (2001).
McLaughlin et al., Adeno-associated virus general transduction vectors: analysis of proviral structures, J. Virol., 62(6):1963-73 (1988).
Meadows et al., Micro-RNA-29 Overexpression by adeno-associated virus suppresses fibrosis in mdx:utrn+/- Mice (S61.003), Neurology. 82:S61.003 (Abstract) (2014).
Meadows et al., Reducing Skeletal Muscle Fibrosis with AAV-Delivered miR-29 (P04.089), Neural., 1 Supplement, (2012).
Melacini et al., Heart involvement in muscular dystrophies due to sarcoglycan gene mutations, Muscle Nerve. 22:473-479 (1999).
Mendell et al., A phase I/2a follistatin gene therapy trial for becker muscular dystrophy, Mol. Ther., 23(1):192-201 (2015).
Mendell et al., Gene Therapy for Spinal Muscular Atrophy Type 1 Shows Potential to Improve Survival and Motor Functional Outcomes, Mol. Ther. 24:S190 (2016).
Mendell et al., Single-Dose Gene-Replacement Therapy for Spinal Muscular Atrophy, N. Engl. J. Med., 377:1713-1722 (2017).
Mendell et al., Sustained alpha-sarcoglycan gene expression after gene transfer in limb-girdle muscular dystrophy, type 2D, Annals of Neural. 68(5):629-638, (Oct. 2010).
Merten, AAV vector production: state of the art developments and remaining challenges, Cell Gene Therapy Insights, 2(5):521-551 (2016).
Moore et al., Limb-girdle muscular dystrophy in the United States, J. Neuropathol. Exp. Neurol., 65(10):995-1003 (2006).

(56) References Cited

OTHER PUBLICATIONS

Moorwood et al., Isometric and eccentric force generation assessment of skeletal muscles isolated from murine models of muscular dystrophies, Journal of Visualized Experiments. 71:e50036 (2013).
Mori et al., Two novel adeno-associated viruses from cynomolgus monkey: pseudotyping characterization of capsid protein, Virology, 330(2):375-383 (2004).
Murphy et al., Long-term correction of obesity and diabetes in genetically obese mice by a single intramuscular injection of recombinant adeno-associated virus encoding mouse leptin, Proc. Natl. Acad. Sci. USA, 94(25):13921-13926 (1997).
Muscat et al., Multiple 5'-flanking regions of the human alpha-skeletal actin gene synergistically modulate muscle-specific expression, Mol. Cell. Biol., 7(11):4089-4099 (1987).
Muzyczka, Use of Adeno-Associated Virus as a General Transduction Vector for Mammalian Cells, Current Topics in Microbiology and Immunology, 158:97-129 (1992).
Narayanaswami et al., Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine, Neurology, 83(16):1453-1463 (2014).
Paul et al., Increased Viral Titer Through Concentration of Viral Harvests from Retroviral Packaging Lines, Human Gene Therapy, 4(5):609-615 (1993).
Perrin et al., An experimental rabies vaccine produced with a new BHK-21 suspension cell culture process: use of serum-free medium and perfusion-reactor system, Vaccine. 13:1244-50 (1995).
Pozsgai et al., —Sarcoglycan gene transfer decreases fibrosis and restores force in LGMD2E mice, Gene Ther. 23:57-66 (2016).
Pozsgai et al., 172. Pre-Clinical Efficacy Study of Beta—Sarcoglycan Gene Transfer, Malec. Ther., 21(1):s68 (2013).
Pozsgai et al., Beta-Sarcoglycan Gene Transfer Leads to Functional Improvement in a Model of LGMD2E (S61.002), Neur., 82(10):1-3 (2014).
Pozsgai et al., β-Sarcoglycan gene transfer decreases fibrosis and restores force in LGMD2E mice, Gene. Ther., 23(1):57-66 (2016).
Pozsgai et al., Systemic AAV-mediated (Beta)-sarcoglycan delivery targeting cardiac and Skeletal muscle ameliorates histological and functional deficits in LGMD2E mice, Mol. Ther. 25(4):855-869 (2017).
Rabinowitz et al., Cross-packaging of a single adeno-associated virus (AAV) type 2 vector genome into multiple AAV serotypes enables transduction with broad specificity, J. Virol. 76:791-801 (2002).
Rafael-Fortney et al., Early treatment with lisinopril and spironolactone preserves cardiac and skeletal muscle in duchenne muscular dystrophy mice, Circulation. 124:582-8 (2011).
Raj Deepak et al., Self-complementary adeno-associated viral vectors for gene therapy of a hemophilia B: progress and challenges, Exert Review of Hemtol. England, Informa Uk, 4(5): 539- 549, (Nov. 2011).
Rodino-Klapac et al., A translational approach for limb vascular delivery of the micro-dystrophin gene without high volume or high pressure for treatment of Duchenne muscular dystrophy, J. Transl. Med., 5:45-55 (2007).
Rodino-Klapac et al., Lack of toxicity of alpha-sarcoglycan overexpression supports clinical gene transfer trial in LGMD2D, Neurology. 71: 240-247 (2008).
Rodino-Klapac et al., Persistent expression of FLAG-tagged micro dystrophin in nonhuman primates following intramuscular and vascular delivery, Mol. Ther. 18:109-117 (2010).
Ruffing et al., Mutations in the carboxy terminus of adeno-associated virus 2 capsid proteins affect viral infectivity: lack of an RGD integrin-binding motif, J. Gen. Virol., 75:3385-3392 (1994).
Salva et al., Design of tissue-specific regulatory cassettes for high-level rAAV-mediated expression in skeletal and cardiac muscle, Mol. Ther., 15(2):320-9 (2007).

Abadi et al., Supplementation with alpha-lipoic acid, CoQ10, and vitamin E augments running performance and mitochondrial function in female mice, PLoS One, 8(4): e60722 (2013).
ABSS (Sequence Alignment; WO2020006458, SEQ ID #1; accessed Mar. 12, 2024) (Year: 2024).
ABSS2 (Sequence Alignment; U.S. Appl. No. 17/255,488, SEQ ID #1; accessed Mar. 12, 2024) (Year: 2024).
Allamand et al., Early adenovirus-mediated gene transfer effectively prevents muscular dystrophy in alpha-sarcoglycan-deficient mice, Gene Ther., 7(16): 1385-91 (2000).
Anderson et al., "Quantitative Filter Hybridisation—Chapter 4", Nucleic acid hyridisation a practical approach, 1985, pp. 73-111.
Arnold et al., Electrophysiological Biomarkers in Spinal Muscular Atrophy: Preclinical Proof of Concept, Ann. Clin. Transl. Neural., 1 (1):34-44 (Jan. 2014).
Asokan et al., The AAV Vector Toolkit: Poised at the Clinical Crossroads; Molecular Therapy, 20(4):699-708 (2012).
Au et al., "Gene therapy advances: a meta-analysis of AAV Usage in Clinical Settings," Frontiers in Medicine, Feb. 9, 2022, vol. 8 (pp. 1-14).
Bang et al., The complete gene sequence of titin, expression of an unusual approximately 700- kDa titin isoform, and its interaction with obscurin identify a novel Z-line to I-band linking system, Gire. Res. 89: 1065-72 (2001).
Bartoli et al., "Safety and efficacy of AAV-mediated calpain 3 gene transfer in a mouse model of limb-girdle muscular dystrophy type 2A", Mol. Ther., 13(2):250-259 (2006).
Bearzi et al., Human cardiac stem cells, Proc. Natl. Acad. Sci. USA. 104:14068-73 (2007).
Behlke, Chemical modification of siRNAs for in vivo use, Oligonucleotides. 18:305-319 (2008).
Belfort et al., Homing endonucleases: from genetic anomalies to programmable genomic clippers Methods Mal. Biol. 1123:1-26 (2014).
Boch et al., Breaking the code of DNA binding specificity of TAL-type III effectors, Science. 326:1509- 12 (2009).
Boissel et al., "megaTALs a rare-cleaving nuclease architecture for therapeutic genome engineering," Nucleic Acids Research, 2014, vol. 42, No. 4 (pp. 2591-2601).
Boissel et al., Assembly and characterization of megaTALs for hyperspecific genome engineering applications, Methods Mal. Biol. 1239: 171-96 (2015).
Bolduc et al., "Recessive Mutations in the Putative Calcium-Activated Chloride Channel Anoctamin 5 Cause Proximal LGMD2L and Distal MMD3 Muscular Dystrophies", The American Journal of Human Genetics, 86, Feb. 12, 2010, (pp. 213-221).
Bouquet et al., Miyoshi-like distal myopathy with mutations in anoctamin 5 gene, Rev. Neural. (Paris), 168(2): 135-41 (Feb. 2012).
Bramsen et al., Development of therapeutic-grade small interfering RNAs by chemical engineering, Front. Genet. 20: 154 (2012).
Ceccadi et al., Homologous recombination-deficient tumors are hyper-dependent on POLQ mediated repair, Nature. 518:258-262 (2015).
Cekaite et al., Gene expression analysis in blood cells in response to unmodified and 2'-modified siRNAs reveals TLR-dependent and independent effects, J. Mal. Biol. 365:90-108 (2007).
Centner et al., Identification of muscle specific ring finger proteins as potential regulators of the titin kinase domain, J. Mal. Biol. 306:717-26 (2001).
Cermak et al., "Efficient design and assembly of custom TALEN and other TAL effector-based constructs for DNA targeting," Nucleic Acids Research, 2011, (pp. 1-11).
Cermak et al., Efficient design and assembly of custom TALENs using the Golden Gate platform, Methods Mal. Biol. 1239: 133-59 (2015).
Ceyhan-Birsoy et al., Recessive truncating titin gene, TTN, mutations presenting as centronucleal myopathy, Neuroloov. 81:1205-14 (2013).
Chandrasekharan et al., Genetic defects in muscular dystrophy, Methods Enzymol. 479:291- 322 (2010).
Chauveau et al., A rising titan: TTN review and mutation update, Human Mutation. 35:1046-59 (2014).

(56) References Cited

OTHER PUBLICATIONS

Chernolovskaya et al., Chemical modification of siRNA, Curr. Opin. Mal. Ther. 12:158-67 (2010).
Chiorini et al., Cloning and characterization of adeno-associated virus type 5, J. Viral., 73(2): 1309-19 (Feb. 1999).
Chiorini et al., Cloning of adeno-associated virus type 4 (AAV4) and generation of recombinant AAV4 particles, J. Viral., 71 (9):6823-33 (Sep. 1997).
Cho et al., DNA repair: Familiar ends with alternative endings, Nature. 518:174-6 (2015).
Cordier et al., "Muscle-Specific Promoters May Be Necessary for Adeno-Associated Virus- Mediated Gene Transfer in the Treatment of Muscular Dystrophies," Human Gene Therapy, Jan. 20, 2001, vol. 12, pp. 205-215.
Cordier et al., "Rescue of Skeletal Muscles of gamma-Sarcoglycan-Deficient Mice with Adeno- Associated Virus-Mediated Gene Transfer," Molecular Therapy, Feb. 2000, vol. 1, No. 2 pp. 119-129.
Cox et al., "Therapeutic genome editing: prospects and challenges," Nature Medicine, Feb. 21, 2015, vol. 2 (pp. 121-131).
D'Amario et al., Functionally competent cardiac stem cells can be isolated from endomyocardial biopsies of patients with advanced cardiomyopathies, Gire. Res. 108:857-61 (2011).
Database Genbank [online], Accession No. AJ277892.2, 2006.11.14 issue.
Daya et al., "Gene Therapy Using Adeno-Associated Virus Vectors," Clinical Microbiology Reviews, Oct. 2008, vol. 21, No. 4 (pp. 583-593).
Deleavey et al., Chemical modification of siRNA, Curr. Protoc. Nucleic Acid Chem. Chapter 16:Unit 16.3 (2009).
Doench et al., "Optimized sgRNA design to maximize activity and minimize off-target effects of CRISPR-Cas9", Nature Biotechnology, Feb. 2016, vol. 34, No. 2 (pp. 184-191).
Dreier et al., "Development of Zinc Finger Domains for Recognition of the 5'-ANN-3' Family of DNA Sequences and Their Use in the Construction of Artificial Transcription Factors," The Journal of Biological Chemistry, Aug. 3, 2001, vol. 276, No. 31 (pp. 29466-29478).
Dreier et al., Insights into the molecular recognition of the 5'-GNN-3' family of DNA sequences by zinc finger domains, J. Mal. Biol. 303:489-502 (2000).
Dreier, B. et al., "Development of zinc finger domains for recognition of the 5'-CNN-3' family DNA sequence and their use in the construction of artificial transcription factors", The Journal of Biological Chemistry, vol. 280, No. 42, Oct. 21, 2005, pp. 35588-3597.
Fanin et al., Gender difference in limb-girdle muscular dystrophy: a muscle fiber morphometric study in 101 patients, Clin. Neuropathology, 33: 179-801 (2014).
Fonfara et al., "Phylogeny of Cas9 determines functional exchangeability of dual-RNA and Cas9 among orthologous type II CRISPR-Cas systems", Nucleic Acids Research, vol. 42, No. 4, Nov. 22, 2013, pp. 2377-2590 (14 pages).
Forbes et al., "Skeletal muscles of ambulant children with Duchenne muscular dystrophy: validation of multicenter study of evaluation with MR imaging and MR spectroscopy", Radiology, 269: 198-207 (2013).
Foye, Whole Genome Sequencing Solved Our Family's Genetic Mystery: Titin, Narrat. Inq. Bioeth 5:206-8 (2015).
Fucini et al., Adenosine modification may be preferred for reducing siRNA immune stimulation, Nucleic Acid Ther. 22:205-210 (2012).
Gaglione et al., Recent progress in chemically modified siRNAs, Mini. Rev. Med. Chem. 10:578-9t (2010).
Gao et al., A novel and efficient model of coronary artery ligation and myocardial infarction in the mouse, Gire. Res. 107:1445-53 (2010).
Gao et al., A novel and efficient model of coronary artery ligation in the mouse, Methods Mal. Bic 1037:299-311 (2013).
Gao et al., Adeno-associated viruses undergo substantial evolution in primates during natural infections, Proc. Natl. Acad. Sci. U.S.A., 2003, vol. 100, pp. 6081-6086.

Gautel et al., The central Z-disk region of titin is assembled from a novel repeat in variable copy Nos., Journal of Cell Science. 109:2747-2754 (1996).
Gebeyehu, et al., "Novel biotinylated nucleotide -- analogs for labeling and colorimetric detection of DNA," Nucleic Acids Research, vol. 15, No. 11, (Jun. 11, 1987), p. 4513-4534.
GenBank Accession No. AF028704.1, Adena-associated virus 6, complete genome, Jan. 12, 1998.
GenBank Accession No. AF028705.1, Adeno-associated virus 3B, complete genome, Jan. 12, 1998.
GenBank Accession No. AX753250.1, Sequence 5 from Patent EP1310571, Jun. 23, 2003.
GenBank Accession No. AY631965.1, Adena-associated virus 10 nonstructural protein and caps protein genes, complete eds, Nov. 30, 2004.
GenBank Accession No. AY631966.1, Adena-associated virus 11 nonstructural protein and caps protein genes, complete eds, Nov. 30, 2004.
GenBank Accession No. DO813647.1, Adena-associated virus 12 Rep78 and VP1 genes, complete eds, Feb. 20, 2008.
GenBank Accession No. EU285562.1, Adena-associated virus 13 nonstructural protein and capsid protein genes, complete eds, Sep. 23, 2008.
GenBank Accession No. NC_001401.2, Adeno-associated virus - 2, complete genome, Aug. 13, 2018.
GenBank Accession No. NC_006152.1, Adeno-associated virus 5, complete genome, Aug. 13, 2018.
GenBank Accession No. NC_006260.1, Adeno-associated virus - 7, complete genome, Aug. 13, 2018.
GenBank Accession No. NC_006261.1, Adeno-associated virus - 8, complete genome, Aug. 13, 2018.
GenBank Accession No. J01901, Adeno-associated virus 2, complete genome, Apr. 27, 1993.
GenBank Accession No. U89790.1, Adeno-associated virus 4, complete genome, Aug. 21, 2017.
GenBank Registered No. NG_011618, Homo sapiens titin (TTN), RefSeqGene (LRG_391) on chromosome 2, Apr. 5, 2020.
Genbank Synthetic construct Homo sapiens clone IMAGE: 100069183, MGC: 199194 anoctamin 5 (ANO5) mRNA, encodes complete protein GenBank: BC172489.1, Mar. 16, 2009.
Gerull et al., Identification of a novel frameshift mutation in the giant muscle filament titin in a large Australian family with dilated cardiomyopathy, J. Mal. Med. (Berl). 84:478-83 (2006).
Gerull et al., Mutations of TTN, encoding the giant muscle filament titin, cause familial dilated cardiomyopathy, Nat. Genet. 30:201-4 (2002).
Goeddel, "Gene Expression Technology: Methods in Enzymology," Academic Press, vol. 185, Jun. 11, 1990, pp. 3-7.
Gombash et al., Adeno-Associated Viral Vector Delivery to the Enteric Nervous System: A Review, Postdoc J., 2015, vol. 3, Issue 8, pp. 1-12.
Govoni et al., "Ongoing therapeutics trials and outcome measures for Duchenne muscular dystrophy", Cell Mol. Life Sci., 70:4585-602 (2013).
Gramlich et al., "Antisense-mediated exon skipping: a therapeutic strategy for titin-based dilated cardiomyopathy," EMBO Molecular Medicine, 7(5): 562-76 (2015).
Gramlich et al., "Stress-induced dilated cardiomyopathy in a knock-in mouse model mimicking human titin-based disease", J. Mal. Cell Cadiol. 47:352-8 (2009).
Granzier et al., "Deleting titin's I-band/A-band junction reveals critical roles for titin in biomechanica sensing and cardiac function", Proc. Natl. Acad. Sci. USA. 111:14589-94 (2014).
Griffin et al., Defective Membrane Fusion and Repair in Anoctamin5-Deficient Muscular Dystrophy', Human Molecular Genetics, vol. 25, No. 10, pp. 1900-1911 (Feb. 23, 2016).
Griffin et al., "Dose-Escalation of Systemically Delivered Adeno-Associated Virus-Mediated alpha-Sarcoglycan in a Mouse Model With Limb-Girdle Muscular Dystrophy Type 2D," Presented at the 2019 Muscular Dystrophy Association Clinical and Scientific Conference, Apr. 13-17, 2019. (Retrieved from: investorrelations.sarepta.com/staticfiles/8b00e773-3b86-4769-83dc-4d2bf22ffb0c).

(56) References Cited

OTHER PUBLICATIONS

Griffin et al., "Systemic Dose Escalation Study of Alpha-Sarcoglycan Provides Functional Improvement in SGCA (I-) Mouse Model of LGMD2D," Molecular Therapy, vol. 26, No. 5S1, May 2018, p. 166.
Grose et al., "Homologous Recombination Mediates Functional Recovery of Dysferlin Deficiency following AAV5 Gene Transfer", PLoS One, Jun. 2012, vol. 7, Issue 6, e39233.
Guilinger et al., "Fusion of catalytically inactive Cas9 to FokI nuclease improves the specificity of genome modification," Nature Biotechnology, vol. 32, No. 6, Jun. 2014 (pp. 577-582).
Gutschner et al., "Genome engineering—Matching supply with demand," Cell Cycle, 15(11): 1395-96 2016.
Hafez et al., "Homing endonucleases: DNA scissors on a mission", Genome. 55:553-69 (2012).
Hagan, "When are mice considered old?" The Jackson Laboratory, https://www.jax.org/news-and-insights/jax-blog/2017/november/when-are-mice-considered-old# Nov. 7, 2017 (8 pages).
Hakim et al., Monitoring murine skeletal muscle function for muscle gene therapy, Methods Mal. Biol., 2011, vol. 709, pp. 75-89.
Handschin et al., Peroxisome proliferator-activated receptor gamma coactivator 1 coactivators, energy homeostasis, and metabolism, Endocrine reviews, 27:728-735 (2002).
Herman et al., "Truncations of titin causing dilated cardiomyopathy", N. Engl. J. Med. 366:619-28, 2012.
Herson et al., A phase I trial of adeno-associated virus serotype 1-gamma-sarcoglycan gene therapy for limb girdle muscular type 2C, Brain, 2012, vol. 135, Pt 2, pp. 483-492.
Hicks et al., A founder mutation in Anoctamin 5 is a major cause of limb-girdle muscular dystrophy, Brain, 134 (Pt. 1): 171-82 (Jan. 2011).
Horii et al., Validation of microinjection methods for generating knockout mice by CRISPR/Cas- mediated genome engineering, Sci Rep. 4:4513 (2014).
International Application No. PCT/US19/39893, International Search Report and Written Opinion, mailed Sep. 25, 2019.
International Application No. PCT/US20/47339, International Preliminary Report on Patentability, mailed Mar. 3, 2022, 8 pages.
International Application No. PCT/US2016/061703, International Preliminary Report on Patentability, mailed May 15, 2018, 10 pages.
International Preliminary Report on Patentability for Appl. Ser. No. PCT/US2016/062052 dated May 22, 2018, 9 pages.
International Preliminary Report on Patentability for Appl. Ser. No. PCT/US2019/039893 dated Dec. 29, 2020 (7 pages).
International Preliminary Report on Patentability on PCT Appl. No. PCT/US2012/066265 dated May 27, 2014 (9 pages).
International Search Report and Written Opinion for Appl. Ser. No. PCTUS2016/061703 dated Feb. 2, 2017 (13 pages).
International Search Report and Written Opinion on PCT Appl. No. PCT/US2020/047339 dated Dec. 10, 2020 (12 pages).
International Search Report and Written Opinion on PCT Appl. No. PCT/US2012/066265 dated Mar. 28, 2013 (7 pages).
International Search Report for Appl. Ser. No. PCT/US2016/062052 dated Feb. 7, 2017 (5 pages).
Itoh-Satoh et al., Titan mutations as the molecular basis for dilated cardiomyopathy, Biochem. Biophys. Res. Commun. 291:385-93 (2002).
Jaber et al., Titin isoforms, extracellular matrix, and global chamber remodeling in experimental dilated cardiomyopathy: functional implications and mechanistic insight, Circ. Heart Fail. 1:192-9 (2008).
Jinek et al., "A Programmable Dual-RNA-Guided DNA Endonuclease in Adaptive Bacterial Immunity," Science, Aug. 17, 2012, 337(6096): 816-821.
John Hopkins Medicine, "Types of Muscular Dystrophy and Neuromuscular diseases," 2023, 6 pages.
Judge et al., "Design of noninflammatory synthetic siRNA mediating potent gene silencing in vivo", Mol. Ther. 13:494-505 (2006).

Justison et al., Percutaneous assisted venous return isolated limb perfusion, J. Extra Corpor. Technol., 2009, vol. 41, Issue 4, pp. 231-234.
Kajigaya et al., Self-assembled B19 parvovirus caps ids, produced in a baculovirus system, are antigenically and immunogenically similar to native virions, Proc. Natl. Acad. Sci. USA, 88(11):4646-50 (Jun. 1991).
Kariko et al., "Suppression of RNA recognition by Toll-like receptors: the impact of nucleoside modification and the evolutionary origin of RNA," Immunity, Aug. 2005, vol. 23 (pp. 165-175).
Kennell, "Principles and Practices of Nucleic Acid Hybridization," Progress in Nucleic Acid Research and Molecular Biology, Academic Press, vol. 11, 1971, (pp. 259-301).
Kent et al., "Mechanism of microhomology-mediated end-joining promoted by human DNA polymerase theta", Nat. Struct. Mol. Biol. 22:230-237 (2015).
Kirnbauer et al., Virus-like particles of bovine papillomavirus type 4 in prophylactic and therapeutic immunization, Virology, 219(1):37-44 (May 1996).
Kleinstiver et al., The I-TevI nuclease and linker domains contribute to the specificity of monomerh TALENs, G3 (Bethesda). 4:1155-65 (2014).
Kole et al., "RNA therapeutics: beyond RNA interference and antisense oligonucleotides", Nat Rev Drug Discov. Jan. 20, 2012;11(2): 125-40. doi: 10.1038/nrd3625.
Kolmerer et al., "Genomic organization of M line titin and its tissue-specific expression in two distinct isoforms", J. Mol. Biol. 256:556-63 (1996).
Kormann et al., "Expression of therapeutic proteins after delivery of chemically modified mRNA in mice," Nature Biotechnology, Feb. 2011, vol. 29, No. 2 (pp. 154-157).
Kornberg et al., "The early history of DNA polymerase: a commentary by Arthur Kornberg", Biochimica et Biophysica Acta. 1000:53-56 (1989).
Kramerova et al., "Null mutation of calpain 3 {p94) in mice causes abnormal sarcomere formation in vivo and in vitro", Hum. Mol. Genet., 13(13): 1373-1388 (2004).
Kramerova et al., Failure to up-regulate transcription of genes necessary for muscle adaptation underlies limb girdle muscular dystrophy 2A calpainopathy, Hum. Mol. Genet., 25(11): 2194-2207 (2016).
Labeit et al., "Titins: giant proteins in charge of muscle ultrastructure and elasticity", Science. 270:293-6 (1995).
Lewinter et al., Cardiac titin and heart disease, J. Cardiovasc. Pharmacol. 63:207-12 (2014).
Lewinter, "Titin isoforms in heart failure: are there benefits to supersizing", Circulation. 110:109-11 2004.
Li et al., "Modularly assembled designer TAL effector nucleases for targeted gene knockout and gene replacement in eukaryotes," Nucleic Acids Research, 2011, vol. 39, No. 14 (pp. 6315-6325).
Li et al., Electrical impedance myography for the in vivo and ex vivo assessment of muscular dystrophy (mdx) mouse muscle, Muscle Nerve, 49(6): 829-35 (Jun. 2014).
Li et al., Electrophysiologic biomarkers for assessing disease progression and the effect of riluzole in SOD1 G93A Als mice, PLoS One, 8(6): e65976 (Jun. 2013).
Li et al., Intracoronary administration of cardiac stem cells in mice: a new, improved technique for cell therapy in murine models, Basic Res. Cardiol. 106:849-64 (2011).
Lin et al., Transcriptional co-activator PGC-1 alpha drives the formation of slow-twitch muscle fibres, Nature, 418:797-801 (2002).
Liu et al., "Validated Zinc Finger Protein Designs for All 16 Gnn Dna Triplet Targets," The Journal of Biological Chemistry, Feb. 8, 2002, vol. 277, No. 6 (pp. 3850-3856).
Louis et al., "EM_EST:BE676391", Jan. 27, 2011 (Jan. 27, 2011), XP055708767, Retrieved from the Internet: URL:http://ibis.internal. epo.org/exam/dbfetch.jsp?id=EM_EST: BE676391 [retrieved on Jun. 25, 2020].
Ma et al., Pol III Promoters to express small RNAs: Delineation of transcription initiation, Mol. Ther. Nucleic Acids. 3:e161 (2014).
Mahmood et al., "Limb-girdle muscular dystrophies: Where next after six decades from the first proposal (review)," Molecular Medicine reports, 2014, vol. 9 (pp. 1515-1532).

(56) References Cited

OTHER PUBLICATIONS

Mak et al., "The crystal structure of TAL effector PthXo1 bound to its DNA target," Science, Feb. 10, 2012, vol. 335, No. 6069 (pp. 716-719).
Makarenko et al., Passive stiffness changes caused by upregulation of compliant titin isoforms in human dilated cardiomyopathy hearts, Gire. Res. 95:708-16 (2004).
Martin et al., Overexpression of Galgt2 in skeletal muscle prevents injury resulting from eccentric contractions in both mdx and wild-type mice, Am. J. Physiol. Cell Physiol., vol. 296, pp. 476-488, Dec. 24, 2008.
Mashiko et al., Generation of mutant mice by pronuclear injection of circular plasmid expressing Cas9 and single guided RNA, Sci. Rep. 3:3355 (2013).
Mateos-Gomez et al., Mammalian Polymerase theta promotes alternative-NHEJ amd suppresses recombination, Nature. 518:254-257 (2015).
Mcnally et al., "Mild and Severe Muscular Dystrophy Caused by a Single gamma-Sarcoglycan Mutation", American Journal of Human Genetics, Nov. 1996, vol. 59, No. 5, pp. 1040-1047.
Mcnally et al., The genetic landscape of cardiomyopathy and its role in heart failure, Cell. Metab. 21:174-182 (2015).
Mendell et al., "Limb-girdle muscular dystrophy type 2D gene therapy restores alpha-sarcoglycan and associated proteins," Ann. Neural., 2009, vol. 66 Issue 3, pp. 290-297.
Mendell et al., Gene Delivery for Limb-Girdle Muscular Dystrophy Type 2D by Isolated Limb Infusion, Human Gene Therapy, 2019, vol. 30, Issue 7, pp. 794-801.
Mingozzi et al. "Therapeutic in vivo gene transfer for genetic disease using AAV: progress and challenges", Nature Reviews Genetics, May 2011, vol. 12 (pp. 341-355).
Monjaret et al., "The Phenotype of Dysferlin-Deficient Mice is not Rescued by Adeno-Associated Virus-Medicated Transfer of Anoctamin 5," Human Gene Therapy Clinical Development, 24(2):65-76 (Jun. 1, 2013).
Moscou et al., "A Simple Cipher Governs DNA Recognition by TAL Effectors", Science, Dec. 11, 2009, vol. 326 (p. 1501).
NCBI Accession No. NG_051363.1, Homo sapiens TTN antisense RNA 1 (TTN-AS1), RefSeqGene on chromosome 2, dated Feb. 17, 2020.
NCBI Accession No. XM_012650762.1, Predicted: Propithecus coquereli titin (TTN), mRNA, dated Jun. 1, 2015.
NCBI Accession No. XM_024453100.1, Predicted: Homo sapiens titin (TTN), transcript variant X12, mRNA, dated Mar. 1, 2020.
NCBI Blast Tool: Pairwise Similarity 1, Instant App ('488) SEQ ID No. 1 [1-3977]: U.S. Pat. No. 9981049B2 SEQ ID No. 8 (CAPN3) (2024).
NCBI Blast Tool: Pairwise Similarity 2, Instant App ('488) SEQ ID No. 1 [1107-3572] :: U.S. Pat. No. 9981049B2 SEQ ID No. 8 (CAPN3) (2024).
NCBI Reference Sequence: "anoctamin-5 isoform a [homo sapiens]", GenPept, Mar. 15, 2015, NP_998764.1.
NCBI, GenBank accession No. U34976.1 (Nov. 8, 1995), 2 pages.
Noguchi S, "Human gamma-sarcoglycan mRNA, complete cds.", NCBI, (Nov. 8, 1995), Database accession No. U34976, 2 pages.
Obermann et al., Molecular structure of the sarcomeric M band: mapping of titin and myosin binding domains in myomesin and the identification of a potential regulatory phosphorylation site in myomesin, EMBO J. 16:211-20 (1997).
Pacak et al., Long-term Skeletal Muscle Protection After Gene Transfer in a Mouse Model of LGMD-2D, Molecular Therapy, 2007, vol. 15, Issue 10, pp. 1775-1781.
Pavlovicova et al., Structure and composition of tubular aggregates of skeletal muscle fibres, Gen. Physiol. Biophys., 22(4):425-40 (Dec. 2003).
Payne et al., Nutritional therapy improves function and complements corticosteroid intervention in mdx mice. Muscle Nerve. Jan. 2006; 33(1):66-77.
Peer et al., Special delivery: targeted therapy with small RNAs, Gene. Ther. 18:1127-33 (2011).

Peled et al., Titin mutation in familial restrictive cardiomyopathy, Int. J. Cardiol. 171:24-30 (2014).
Penttila et al., Eight new mutations and the expanding phenotype variability in muscular dystrophy caused by ANOS, Neurology, 78(12):897-903 (Mar. 2012).
Powers et al., Exercise-induced oxidative stress in humans: cause and consequences, Free Radic. Biol. Med., 51 (5):942-50 (Sep. 2011).
Ran et al., "In vivo genome editing using Staphylococcus aureus Cas9," Nature, April, 9, 2015, vol. 520, (18 pages).
Richard et al., "Mutations In The Proteolytic Enzyme Calpain 3 Cause Limb-Girdle Muscular Dystrophy Type 2A", Cell, 81(1):27-40 (1995).
Roberts et al., Integrated allelic, transcriptional, and phenomic dissection of the cardiac effects of titin truncations in health and disease, Sci. Transl. Med. 7:270ra6 (2015).
Rodino-Klapac et al., "Micro-dystrophin and follistatin co-delivery restores muscle function in aged DMD model," Human Molecular Genetics, Dec. 2013, vol. 22, No. 24 (pp. 4929-4937).
Rodino-Klapac et al., Demonstration of SGCA Expression and Related Outcomes in Phase I/IIa Safety Isolated Limb Perfusion Trial in LGMD2D Subjects, Molecular Theerapy, 2018, vol. 26, Issue 5, Supplemental 1, p. 1, Abstract No. 250.
Rose, comprehensive Virology 3:1-61 (1974).
Roudaut et al., "Restriction of Calpain3 Expression to the Skeletal Muscle Prevents Cardiac Toxicity and Corrects Pathology in a Murine Model of Limb-Girdle Muscular Dystrophy", Circulation, 128(10): 1094-1104, (Sep. 2013).
Rutledge et al., Infectious clones and vectors derived from adeno-associated virus (AAV) serotypes other than AAV type 2, J. Viral., 7291): 309-19 (Jan. 1998).
Sahenk et al., Systemic delivery of AAVrh74.tMCK.hCAPN3 rescues the phenotype in a mouse model for LGMD2A/R1, Mol. Ther. Methods Clin. Dev., 22:401-414 (2021).
Sambrook et al., Molecular Cloning: A Laboratory Manual, 2 edition (1989).
Sander et al., CRISPR-Cas systems for editing, regulating and targeting genomes, Nat. Biotechnol. 32:347-55 (2014).
Sanganalmath et al., Cell therapy for heart failure: a comprehensive overview of experimental and clincal studes, current challenges, and future directions, Gire. Res. 113:810-34 (2013).
Schreiber et al., The transcriptional coactivator PGC-1 regulates the expression and activity of the orphan nuclear receptor estrogen-related receptor alpha (ERRalpha), J. Biol. Chem., 278: 9013-9018 (2003).
Segal et al., "Toward controlling gene expression at will: Selection and design of zinc finger domains recognizing each of the 5'-GNN-3' Dna target sequences," Proceedings of the National Academy of Sciences, USA, Mar. 1999, vol. 96 (pp. 2758-2763).
Shih et al., Finding the Achilles' heel of Muscle Giant-TALEN-mediated Gene-editing in Zebrafish Titin', Circulation Research, Oct. 21, 2015, vol. 117, no.(suppl_1), pages A344. DOI: https://doi.org/10.1161/res. 117.suppl_1.344.
Siu et al., Familial dilated cardiomyopathy locus maps to chromosome 2q31, Circulation. 99:1022-6 (1999).
Smith et al., Modification and secretion of human interleukin 2 produced in insect cells by a baculovirus expression vector, Proc. Natl. Acad. Sci. USA, 82(24): 8404-8 (1985).
Sondergaard et al., "AAV.Dysferlin Overlap Vectors Restore Function in Dysferlinopathy Animal Models," Annals of Clinical and Translational Neurology, 2015, vol. 2, Issue 3, pp. 256-270.
Sonntag et al., A viral assembly factor promotes AAV2 capsid formation in the nucleolus, PNAS,2010, vol. 107, Issue 22, p. 10220-10225.
Sorimachi et al., Tissue-specific expression and alpha-actinin binding properties of the Z-disc titin: implications for the nature of vertebrate Z-discs, J. Mal. Biol. 270:688-95 (1997).
Soutschek et al., "Therapeutic silencing of an endogenous gene by systemic administration of modified siRNAs," Nature, Nov. 2004, pp. 173-178, vol. 432.
Steentoft et al., Precision genome editing: a small revolution for glycobiology, Glycobiology. 24:663- 80 (2014).

(56) References Cited

OTHER PUBLICATIONS

Strobel, et al. "Antioxidant Supplementation Reduces Skeletal Muscle Mitochondrial Biogenesis", Official Journal of the American College of Sports Medicine, 2011, pp. 1017-1024.
Thiruvengadam et al., "Anoctamin 5 Knockout Mouse Model Recapitulates LGMD2L Muscle Pathology and Offers Insight Into in vivo Functional Deficits," Journal of Neuromuscular Diseases, 2021, vol. 8 (S243-S255).
Torella, et al., "Cardiovascular development: towards biomedical applicability; Resident cardiac stem cells", CMLS Cellular and Molecular Life Sciences 64(6): 661-673 (2007).
Tsai et al., "GUIDE-seq enables genome-wide profiling of off-target cleavage by CRISPR-Cas nucleases," Nature Biotechnology, Feb. 2015, vol. 33, No. 2 (pp. 187-197).
Tsai et al., Dimeric CRISPR RNA-guided FokI nucleases for highly specific genome editing, Nat. Biotechnol. 32:569-76 (2014).
Van Akkooi et al., Isolated limb perfusion for an irresectable melanoma recurrence in a Jehovah's witness, Eur. J. Cardiothorac. Surg., 2006, vol. 30, Issue 2, pp. 408-410.
Volkov et al., Selective protection of nuclease-sensitive sites in siRNA prolongs silencing effect, Oligonucleotides. 19:191-202 (2009).
Wang et al., "The potential of adeno-associated viral vectors for gene delivery to muscle tissue", Exp. Opin. on Drug. Del., 11(3):345-364 (2014).
Wang et al., Rapid and efficient assembly of transcription activator-like effector genes by USER cloning, J. Genet. Genomics. 41:339-47 (2014).
Wang et al., Recombinant AAV serotype 1 transduction efficiency and tropism in the murine brain, Gene Ther., 2003, vol. 10, Issue 17, pp. 1528-1534.
Watson et al., "Recombinant DNA," Scientific American, Second Edition, 2001 (pp. 153-154).
Weber et al., "A Modular Cloning System for Standardized Assembly of Multigene Constructs," Feb. 2011, vol. 6, No. 2, e16765 (11 pages).
Whitehead et al., Silencing or stimulation? siRNA delivery and the immune system, Annual Review of Chemical and Biomolecular Engineering. 2:77-96 (2011).
Wikipedia, "Adeno-associated virus," downloaded Dec. 29, 2017 (pp. 1-18).
Wikipedia, "Limb-girdle muscular dystrophy," 11 pages, Retrieved Oct. 26, 2023, from https://en.wikipedia.org/wiki/Limb-girdle_muscular_dystrophy (11 pages).
Winkler, Oligonucleotide conjugates for therapeutic applications, Ther. De/iv. 4:791-809 (2013).
Witting et al.: "Anoctamin 5 muscular dystrophy in Denmark: prevalence, genotypes, phenotypes, cardiac findings, and muscleprotein expression", Case Reports, May 14, 2013, PMID:23670307 DOI: 10.1007/s00415-013-6934-y.
Wolfs et al., MegaTevs: single-chain dual nucleases for efficient gene disruption, Nucliec Acids Res. 42:8816-29 (2014).
Wu et al., Mutational analysis of the adeno-associated virus type 2 (AAV2) capsid gene and construction of AAV2 vectors with altered tropism, J. Viral., 74(18): 8635-47 (Sep. 2000).
Xu et al., "Genetic disruption of Ano5 in mice does not recapitulate human ANO5-deficient muscular dystrophy," Skeletal Muscle, 2015, vol. 5, No. 43 (pp. 1-14).
Xu et al., Postnatal overexpression of the CT GalNAc transferase inhibits muscular dystrophy in mdx mice without altering muscle growth or neuromuscular development: evidence for a utrophin-independent mechanism, Neuromuscul. Disord., 2007, vol. 17, Issue 3, pp. 209-220.
Yalvac et al., Impaired regeneration in calpain-3 null muscle is associated with perturbations in mTORC1 signaling and defective mitochondrial biogenesis, Skelet. Muscle, 7:27, 18 pages (2017).
Yan et al., Inverted terminal repeat sequences are important for intermolecular recombination and circularization of adeno-associated virus genomes, J. Viral., 79(1):364-79 (Jan. 2005).
Yuasa et al., "Gene therapy of muscular dystrophy: Systemic gene delivery to skeletal muscles" Jan. 2007, Drug Delivery System 22(2): 140-147, doi.org/10.2745/dds.22. 140 (English Abstract).
Zetsche at el., "Cpfl Is a Single RNA-Guided Endonuclease of a Class 2 CRISPR-Cas System," Cell, Oct. 22, 2015, vol. 163, No. 3 (pp. 759-771).
Zhao et al., BPV1 E2 protein enhances packaging of full-length plasmid DNA in BPV1 pseudovirions, Virology, 272(2): 382-93 (Jul. 2000).
Zhou et al., Pressure Overload by Transverse Aortic Constriction Induces Maladaptive Hypertrophy in a Titin-Truncated Mouse Model, Biomed. Res. Int. 2015: 163564 (2015).
Zou et al., "An internal promoter underlies the difference in disease severity between N- and C- terminal truncation mutations of Titin in zebrafish", eLife, Oct. 16, 2015, vol. 4, pages e09406. DOI: https://doi.org/10.7554/eLife.09406.
Dorange et al., "Analytical approaches to characterize AAV vector production & purification: Advances and challenges," Cell & Gene Therapy Insights, 4(2): 119-129 (2018).
Hou et al., "Serious Overestimation in Quantitative PCR by Circular (Supercoiled) Plasmid Standard: Microalgal pcna as the Model Gene," PLOS One 5(3): e9545, 8 pages (Mar. 5, 2010) doi:10.1371/journal.pone.0009545.
Martinez-Fernandez de la Camara et al., "The accurate quantification of AAV genomic titre depends on the conformation of the plasmid reference," ARVO Annual Meeting Abstract, 3 pages, Jul. 2018.
Wu et al., "Adeno-associated virus serotypes: vector toolkit for human gene therapy." Molecular therapy 14.3 (2006): 316-327 (Year: 2006).
Pozsgai et al., "506. [beta] —Sarcoglycan Gene Transfer Prevents Muscle Fibrosis and Inflammation in an Aged LGMD2E Mouse Model," Molecular Therapy, vol. 23 Supplement 1, May 2015, 2 pages.
Werling et al., "Systematic comparison and validation of quantitative real-time PCR methods for the quantitation of adeno-associated viral products," Human Gene Therapy Methods, 26.3:82-92 (Jun. 2015).
Thomas et al., "B4GALNT2 (GALGT2) Gene Therapy Reduces Skeletal Muscle Pathology in the FKRP P448L Mouse Model of Limb Girdle Muscular Dystrophy 21", Am. J_ Pathol., 186(9):2429-2448 (2016).
Chu et al., "The limb-girdle muscular dystrophies: is treatment on the horizon?" Neurotherapeutics, 15(4): 849-862 (Oct. 2018).
Monies et al., "A first-line diagnostic assay for limb-girdle muscular dystropy and other nyopathies", Human Genomics, 10(1):32, pp. 1-7 (Sep. 27, 2016).
Theadom et al., "Prealence of muscular dystrophies: a systematic literature review," Neuroepidemiology 43(3-4):259-68 (2014).
Wagner et al., "A novel method for the quantification of adeno-associated virus vectors for RNA interference applications using quantitative polymerase chain reaction and purified genomic adeno-associated virus DNA as a standard," Human Gene Therapy Methods, 24(6): 355-63 (Dec. 2013).
Walter et al., "Recent developments in Duchenne muscular dystrophy: facts and numbers," Journal of Cachexia, Sarcopenia and Muscle, 8(5):681-685 (Oct. 2017).

\* cited by examiner

Fig. 2A

Length: 4511 (SEQ ID NO: 1)

3'ITR   (5' SEQ ID NO: 8, 3' SEQ ID NO: 15)

PolyA  (5' SEQ ID NO: 6, 3' SEQ ID NO: 14)

Beta-sarcoglycan cDNA sequence (5' SEQ ID NOS: 11, 3' SEQ ID NO: 2)

*chimeric intron sequence* (5' SEQ ID NO: 4, 3'SEQ ID NO: 12)

MHCK7  (5' SEQ ID NO: 5, 3' SEQ ID NO: 13)

5' ITR (SEQ ID NO: 7)

Hairpin (SEQ ID NO: 10)

```
  1 CTGCGCGCTC GCTCGCTCAC TGAGGCCGCC CGGGCAAAGC CCGGGCGTCG
 51 GGCGACCTTT GGTCGCCCGG CCTCAGTGAG CGAGCGAGCG CGCAGAGAGG
101 GAGTGGCCAA CTCCATCACT AGGGGTTCCT TGTAGTTAAT GATTAACCCG
151 CCATGCTACT TATCTACGTA GCCATGCTCT AGAGGCGCGC CCCTGCAGGA
201 CACACAAAAA ACCAACACAC AGATCTAATG AAAATAAAGA TCTTTTATTG
251 CGGCCAAGCT TTTAATGAGT ATTCCCACAA GGGTTATCGC TAATCTGACA
301 TCCCATATTC TGGCTGGTGA CCTGCACTTT AAACAGGGTG CCATCGGCAC
351 ACATGCACAG CTTATACCTG ACCCAATCTC CGGACCCCAG CTGGTCTCCA
401 CTAGAGGAGC TGGGCAGTCT GGTAGTGGAG ACCATCACGC TCCCATTCAG
451 AATGATGCTG TTTTCTGCTT TCAGCTCCAT GTTGCCTCCC ATGTGAAATT
501 CAATTGTCTT GCCCATGATG AACACGCCCT CATTTCCCCG GACAATAGCT
551 CGTCCATCCA CCTTGATATT CAGGTCTGAT GTAGCGTTAC TGGTGATTCT
601 CTCAGTGCTG GCTTTCTGGA CGTTCAGAGA CTTCACCCCG GAAGGCAGAT
651 GAAATTCGTG TGTCTCATAG TCGGTACTGA ACAGGATATT CTGGGTCCGG
701 GGATCAAAGA ACTGCATGCC AATGTCGCTA GTGATTGATG TTTTATTGTT
751 TTCCACAGAC AGCTTTGTGG TTCCCTGCTG GAACACAATG GGCTGATTGT
```

Fig. 2B

```
 801 TCCCGGTGAT CACCAGATTC TCGTTTCTCC GCCCGCCGAC AGTAGATTTG
 851 TACAGTGGAT GGATGACCCC CATATCGGAC ACCTGCTTAA ATCGCAGCAG
 901 GCCACTTTCG TGGAACTCCA TAGAGTCACA CCCGTTTGGG CCAATGCGGA
 951 TGACAGCCCA ATCACCAGA GTAATGATCA GATTAATCAC GGCCAGGATA
1001 AACAGCAGAA TGATGACGCA GATTGCCAGG TTTCCTTTGC GCCCCCTCAG
1051 GCCTGTCTTA TGCAGGCGAT CTTCGTCAAT AGGGATGTAG CCGGCTTTGA
1101 AATTGCTGTT GTGCTCCTTA TTCACTGATC TCCTCTCGAC GGCTTTTTCT
1151 CTCATTGATT TTTTCACTGG TCCATTGCTT GACTGCTGCT CGGCGGCTGC
1201 GGCGGCTGCT GCTGCCATGG TGGTACC***GGG TACAATTCCG CAGCTTTTAG***
1251 *AGCAGAAGTA ACACTTCCGT ACAGGCCTAG AAGTAAAGGC AACATCCACT*
1301 *GAGGAGCAGT TCTTTGATTT GCACCACCAC CGGATCCGGG ACCTGAAATA*
1351 *AAAGACAAAA AGACTAAACT TACCT*GGGCG CGCCGCTGGC TGCTCCTGAG
1401 TGTCTGTCTG TGCTGTGGAG GTGGTGGTAG AATGAGGGCA GCCCCTGTGC
1451 CCCTGGGTTA TATAGAGGAG CCTACAGGGT GTGACTAGCC AGGAGGGGCT
1501 GTCCCCAGGG AGGGGCCCCT GAGAGCAGAT GAGCTTTCAG CTCGTTGCCC
1551 GGGCACCGTG CCCACCCCGG ACCCAGGCGT GCAGCTTGCC CAGCCCCATG
1601 GCCTTGTATG GGCTGCCCCA AGGGCTGACT TGCTCACTGG TTCCTAAACT
1651 AAGTGCTGAG TCTAGCTGGC GGGGACAGC TGGCCCTTCG CCGGGAACAT
1701 GGAACAGTAA TACTTTGGGA GTCCCAGGCA CGTATAAGCC CTGGCCCCCA
1751 AGCCTGTTAC AGCCTGCCCT CAGTCCCCCA CAGCCTTGTT CGAAGATCTT
1801 CGCATGCAGG GGATCCACCA GGGACAGGGT TATTTTTAGA GGCAGCAGGT
1851 GTTGGGGGGG GGGGGCAGC CACATGTCTG GGTTAATTAT AACCAGGCAT
1901 CTCGGGTGTC CCCAGGCCTT GCCTCCTTAC ATGGGCAGCC TAGACCCGTA
1951 GTGGGGCATG CTAGACAGCA GGGCCCCAAG GTTTGCCCAT GAAAGGTCTG
2001 TTGCCCTCGC CCCTCTGGCT CCATGGCCTT TTTTTAGTCC TTGGGCACAT
2051 TCCTCCTCCC CAAAGGGCCG ATGGGCAGAT AGAGGAGAGA CAGGAGCGTC
2101 TCACACCACC TCCCCTACCC AGGCCCTTAC CTCAGTTATT TTTAATCTGA
```

Fig. 2C

```
2151 AGGGTCTAGC TTAGACATGC AAGCTTGCGG CCGCCAATTG GTTAACCCCA
2201 CTCCCTCTCT GCGCGCTCGC TCGCTCACTG AGGCCGCCCG GGCAAAGCCC
2251 GGGCGTCGGG CGACCTTTGG TCGCCCGGCC TCAGTGAGCG AGCGAGCGCG
2301 CAGAGAGGGA GTGGGGTTAA CCAATTGGCG GCCGCAAGCT TGCATGTCTA
2351 AGCTAGACCC TTCAGATTAA AAATAACTGA GGTAAGGGCC TGGGTAGGGG
2401 AGGTGGTGTG AGACGCTCCT GTCTCTCCTC TATCTGCCCA TCGGCCCTTT
2451 GGGGAGGAGG AATGTGCCCA AGGACTAAAA AAAGGCCATG GAGCCAGAGG
2501 GGCGAGGGCA ACAGACCTTT CATGGGCAAA CCTTGGGGCC CTGCTGTCTA
2551 GCATGCCCCA CTACGGGTCT AGGCTGCCCA TGTAAGGAGG CAAGGCCTGG
2601 GGACACCCGA GATGCCTGGT TATAATTAAC CCAGACATGT GGCTGCCCCC
2651 CCCCCCCCAA CACCTGCTGC CTCTAAAAAT AACCCTGTCC CTGGTGGATC
2701 CCCTGCATGC GAAGATCTTC GAACAAGGCT GTGGGGGACT GAGGGCAGGC
2751 TGTAACAGGC TTGGGGGCCA GGGCTTATAC GTGCCTGGGA CTCCCAAAGT
2801 ATTACTGTTC CATGTTCCCG GCGAAGGGCC AGCTGTCCCC CGCCAGCTAG
2851 ACTCAGCACT TAGTTTAGGA ACCAGTGAGC AAGTCAGCCC TTGGGGCAGC
2901 CCATACAAGG CCATGGGGCT GGGCAAGCTG CACGCCTGGG TCCGGGGTGG
2951 GCACGGTGCC CGGGCAACGA GCTGAAAGCT CATCTGCTCT CAGGGGCCCC
3001 TCCCTGGGGA CAGCCCCTCC TGGCTAGTCA CACCCTGTAG GCTCCTCTAT
3051 ATAACCCAGG GGCACAGGGG CTGCCCTCAT TCTACCACCA CCTCCACAGC
3101 ACAGACAGAC ACTCAGGAGC AGCCAGCGGC GCGCCCAGGT AAGTTTAGTC
3151 TTTTTGTCTT TTATTTCAGG TCCCGGATCC GGTGGTGGTG CAAATCAAAG
3201 AACTGCTCCT CAGTGGATGT TGCCTTTACT TCTAGGCCTG TACGGAAGTG
3251 TTACTTCTGC TCTAAAAGCT GCGGAATTGT ACCCGGTACC ACCATGGCAG
3301 CAGCAGCCGC CGCAGCCGCC GAGCAGCAGT CAAGCAATGG ACCAGTGAAA
3351 AAATCAATGA GAGAAAAGC CGTCGAGAGG AGATCAGTGA ATAAGGAGCA
3401 CAACAGCAAT TTCAAAGCCG GCTACATCCC TATTGACGAA GATCGCCTGC
3451 ATAAGACAGG CCTGAGGGGG CGCAAAGGAA ACCTGGCAAT CTGCGTCATC
3501 ATTCTGCTGT TTATCCTGGC CGTGATTAAT CTGATCATTA CTCTGGTGAT
```

Fig. 2D

```
3551 TTGGGCTGTC ATCCGCATTG GCCCAAACGG GTGTGACTCT ATGGAGTTCC
3601 ACGAAAGTGG CCTGCTGCGA TTTAAGCAGG TGTCCGATAT GGGGGTCATC
3651 CATCCACTGT ACAAATCTAC TGTCGGCGGG CGGAGAAACG AGAATCTGGT
3701 GATCACCGGG AACAATCAGC CCATTGTGTT CCAGCAGGGA ACCACAAAGC
3751 TGTCTGTGGA AAACAATAAA ACATCAATCA CTAGCGACAT TGGCATGCAG
3801 TTCTTTGATC CCCGGACCCA GAATATCCTG TTCAGTACCG ACTATGAGAC
3851 ACACGAATTT CATCTGCCTT CCGGGGTGAA GTCTCTGAAC GTCCAGAAAG
3901 CCAGCACTGA GAGAATCACC AGTAACGCTA CATCAGACCT GAATATCAAG
3951 GTGGATGGAC GAGCTATTGT CCGGGGAAAT GAGGGCGTGT TCATCATGGG
4001 CAAGACAATT GAATTTCACA TGGGAGGCAA CATGGAGCTG AAAGCAGAAA
4051 ACAGCATCAT TCTGAATGGG AGCGTGATGG TCTCCACTAC CAGACTGCCC
4101 AGCTCCTCTA GTGGAGACCA GCTGGGGTCC GGAGATTGGG TCAGGTATAA
4151 GCTGTGCATG TGTGCCGATG GCACCCTGTT TAAAGTGCAG GTCACCAGCC
4201 AGAATATGGG ATGTCAGATT AGCGATAACC CTTGTGGGAA TACTCATTAA
4251 AAGCTT*GGCC GCAATAAAAG ATCTTTATTT TCATTAGATC TGTGTGTTGG*
4301 *TTTTTTGTGT* GTCCTGCAGG GGCGCGCCTC TAGAGCATGG CTACGTAGAT
4351 AAGTAGCATG GCGGGTTAAT CATTAACTAC AAGGAACCCC TAGTGATGGA
4401 GTTGGCCACT CCCTCTCTGC GCGCTCGCTC GCTCACTGAG GCCGGGCGAC
4451 CAAAGGTCGC CCGACGCCCG GCTTTGCCC GGGCGGCCTC AGTGAGCGAG
4501 CGAGCGCGCA G
```

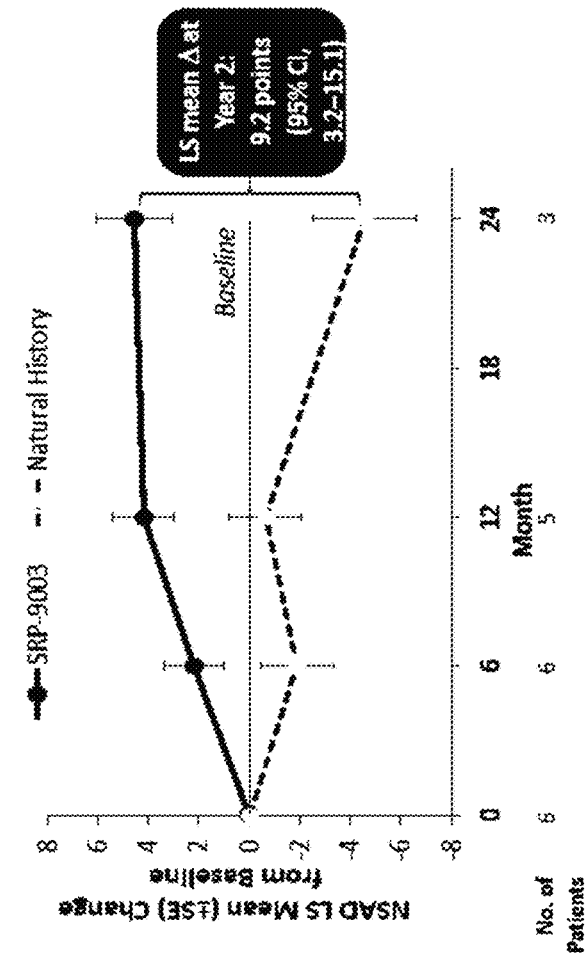
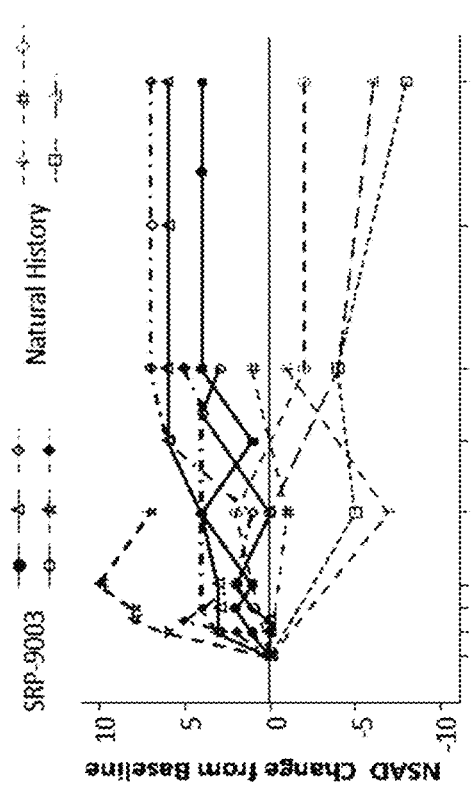
Fig. 7

SEQUENCE LISTING

Sequence total quantity: 15
SEQ ID NO: 1           moltype = DNA  length = 4511
FEATURE                Location/Qualifiers

```
misc_feature       1..4511
                   note = scAAV construct sequence
source             1..4511
                   mol_type = other DNA
                   organism = synthetic construct
SEQUENCE: 1
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
agggggttcct tgtagttaat gattaacccg ccatgctact tatctacgta gccatgctct    180
agaggcgcgc ccctgcagga cacacaaaaa accaacacac agatctaatg aaaataaaga     240
tctttttattg cggccaagct tttaatgagt attcccacaa gggttatcgc taatctgaca    300
tcccatattc tggctggtga cctgcacttt aaacagggtg ccatcggcac acatgcacag    360
cttatacctg acccaatctc cggaccccag ctggtctcca ctagaggagc tgggcagtct    420
ggtagtggag accatcacgc tcccattcag aatgatgctg ttttctgctt tcagctccat    480
gttgcctccc atgtgaaatt caattgtctt gcccatgatg aacacgccct catttccccg    540
gacaatagct cgtccatcca ccttgatatt caggtctgat gtagcgttac tggtgattct    600
ctcagtgctg gctttctgga cgttcagaga cttcaccccg gaaggcagat gaaattcgtg    660
tgtctcatag tcggtactga acaggatatt ctgggtccgg ggatcaaaga actgcatgcc    720
aatgtcgcta gtgattgatg ttttattgtt ttccacagac agctttgtgg ttccctgctg    780
gaacacaatg ggctgattgt tcccggtgat caccagattc tcgtttctcc gcccgccgac    840
agtagatttg tacagtggat ggatgacccc catatcggac acctgcttaa atcgcagcag    900
gccactttcg tggaactcca tagagtcaca cccgtttggg ccaatgcgga tgacagccca    960
aatcaccaga gtaatgatca gattaatcac ggccaggata aacagcagaa tgatgacgca   1020
gattgccagg tttcctttgc gcccctcag gcctgtctta tgcaggcgat cttcgtcaat    1080
agggatgtag ccgctttga aattgctgtt gtgctcctta ttcactgatc tcctctcgac     1140
ggcttttct ctcattgatt ttttcactgg tccattgctt gactgctgct cggcggctgc    1200
ggcggctgct gctgccatgg tggtaccggg tacaattccg cagcttttag agcagaagta    1260
acacttccgt acaggcctag aagtaaaggc aacatccact gaggagcagt tctttgattt    1320
gcaccaccac cggatccggg acctgaaata aaagacaaaa agactaaact tacctgggcg    1380
cgccgctggc tgctcctgag tgtctgtctg tgctgtggag gtgggtggtag aatgagggca   1440
gccctgtgc ccctgggtta tatagaggag cctacagggt gtgactagcc aggagggggct   1500
gtccccaggg aggggcccct gagagcagat gagctttcag ctcgttgccc gggcaccgtg   1560
cccaccccgg acccaggcgt gcagcttgcc cagccccatg gccttgtatg ggctgcccca   1620
agggctgact tgctcactgg ttcctaaact aagtgctgag tctagctggc gggggacagc   1680
tggcccttcg ccgggaacta ggaacagtaa tactttgtga gtcccaggca cgtataagcc   1740
ctggcccca agcctgttac agcctgccct cagtccccca cagccttgtt cgaagatctt    1800
cgcatgcagg ggatccacca gggacagggt tatttttaga ggcagcaggt gttgggggg    1860
ggggggcagc cacatgtctg ggttaattat aaccaggcat ctcgggtgtc cccaggcctt   1920
gcctccttac atgggcagcc tagacccgta gtgggggcatg ctagacagca gggccccaag   1980
gtttgcccat gaaaggtctg ttgccctcgc ccctctggct ccatggcctt tttttagtcc    2040
ttgggcacat tcctcctccc caaagggccg atgggcagat agaggagaga caggagcgtc    2100
tcacaccacc tcccctaccc aggcccttac ctcagttatt tttaatctga agggtctagc    2160
ttagacatgc aagcttgcgg ccgccaattg gttaaccca ctccctctct gcgcgctcgc      2220
tcgctcactg aggccgcccg ggcaaagccc gggcgtcggg cgacctttgg tcgcccggcc    2280
tcagtgagcg agcgagcgcg cagagaggga gtggggttaa ccaattggcg gccgcaagct    2340
tgcatgtcta agctagaccc ttcagattaa aaataactga ggtaagggcc tgggtagggg    2400
aggtggtgtg agacgtcct gtctctcctc tatctgccca tcggccctt ggggaggagg     2460
aatgtgccca aggactaaaa aaaggccatg gagccagagg ggcgagggca acagacccttt   2520
catgggcaaa cctggggcc ctgctgtcta gcatgcccca ctacgggtct aggctgccca     2580
tgtaaggagg caaggcctgg ggacacccga gatgcctggt tataattaac ccagacatgt    2640
ggctgccccc cccccccaa cacctgctgc ctctaaaaat aaccctgtcc ctggtggatc     2700
ccctgcatgc gaagatcttc gaacaaggct gtgggggact gagggcaggc tgtaacaggc    2760
ttgggggcca gggcttatac gtgcctggga ctcccaaagt attactgttc catgttcccg    2820
gcgaagggcc agctgtcccc cgccagctag actcagcact tagtttagga accagtgagc    2880
aagtcagccc ttggggcagc ccatacaagg ccatgggcct gggcaagctg cacgcctggg    2940
tccggggtgg gcacggtgcc cgggcaacga gctgaaagct catctgctct caggggcccc    3000
tccctgggga cagcccctcc tggctagtca cacccctgtag gctcctctat ataacccagg    3060
ggcacagggg ctgccctcat tctaccacca cctccacagc acagacagac actcaggagc   3120
agccagcggc gcgcccaggt aagtttagtc tttttgtctt ttatttcagg tcccggatcc   3180
ggtggtggtg caaatcaaag aactgctcct cagtggatgt tgcctttact tctaggcctg   3240
tacgaagtg ttacttctgc tctaaaagct gcggaattgt acccggtacc accatgcag     3300
cagcagccgc cgcagccgcc gagcagcagt caagcaatgg accagtgaaa aaatcaatga    3360
gagaaaaagc cgtcgagagg agatcagtga ataaggagca caacagcaat ttcaaagccg    3420
gctacatccc tattgacgaa gatcgcctgc ataagacagg cagagggga cgcaagaaga    3480
acctggcaat ctgcgtcatc attctgctgt ttatcctggc cgtgattaat ctgatcatta    3540
ctctggtgat tgggctgtc atccgcattg gcccaaacgg tgtgactct atggagttcc     3600
acgaaagtgt cctgctgcga tttaagcagg tgtccgatat ggggggtcatc catccactgt    3660
acaaatctac tgtcggcggg cggagaacga agatctggtt gatcaccggg aacaatcagc    3720
ccattgtgtt ccagcaggga aaccacaaagc tgtctgtgga aaacaataaa acatcaatca    3780
ctagcgacat tggcatgcag ttctttgatc cccggaccca gaatatcctg ttcagtaccg    3840
actatgagac acacgaattt catctgcctt ccggggtgaa gtctctgaac gtccagaaag    3900
ccagcactga gagaatcacc agtaacgcta catcagacct gaatatcaag gtggatggac    3960
gagctattgt ccggggaaat gagggcgtgt tcatcatggg caagacaatt gaatttcaca    4020
tgggaggcaa catggagctg aaagcagaaa acagcatcat tctgaatggg agtcgtgttg    4080
tctccactac cagactgccc agctcctcta gtgagaacca gctggggtcc ggagattggg    4140
tcaggtataa gctgtgcatg tgtgccgatg gcacccgtt taaagtgcag gtcaccagcc    4200
agaatatggg atgtcagatt agcgataacc ttgtgggaa tactcattaa aagcttggcc    4260
gcaataaaag atctttattt tcattagatc tgtgtgttgg ttttttgtgt gtcctgcagg    4320
ggcgcgcctc tagagcatgg ctacgtagat aagtagcatg gcgggttaat cattaactac    4380
```

```
aaggaacccc tagtgatgga gttggccact ccctctctgc gcgctcgctc gctcactgag  4440
gccgggcgac caaaggtcgc ccgacgcccg ggctttgccc gggcggcctc agtgagcgag  4500
cgagcgcgca g                                                      4511

SEQ ID NO: 2           moltype = DNA   length = 957
FEATURE                Location/Qualifiers
source                 1..957
                       mol_type = other DNA
                       organism = Homo sapiens
SEQUENCE: 2
atggcagcag cagccgccgc agccgccgag cagcagtcaa gcaatggacc agtgaaaaaa   60
tcaatgagag aaaaagccgt cgagaggaga tcagtgaata aggagcacaa cagcaatttc  120
aaagccggct acatccctat tgacgaagat cgcctgcata agacaggcct gaggggggcgc  180
aaaggaaacc tggcaatctg cgtcatcatt ctgctgttta tcctggccgt gattaatctg  240
atcattactc tggtgatttg ggctgtcatc cgcattggcc caaacgggtg tgactctatg  300
gagttccacg aaagtggcct gctgcgattt aagcaggtgt ccgatatggg ggtcatccat  360
ccactgtaca atctactgt cggcgggcgg agaaacgaga tctggtgat caccgggaac  420
aatcagccca ttgtgttcca gcaggaacc acaaagctgt ctgtgaaaa caataaaaca  480
tcaatcacta gcgacattgg catgcagttc tttgatcccc ggacccagaa tatcctgttc  540
agtaccgact atgagacaca cgaatttcat ctgccttccg gggtgaagtc tctgaacgtc  600
cagaaagcca gcactgagag aatcaccagt aacgctacat cagacctgaa tatcaaggtg  660
gatgacgag ctattgtccg gggaaatgag ggcgtgttca tcatgggcaa gacaattgaa  720
tttcacatgg gaggcaacat ggagctgaaa gcagaaaaca gcatcattct gaatgggagc  780
gtgatggtct ccactaccag actgcccagc tcctctagtg gagaccagct ggggtccgga  840
gattgggtca ggtataagct gtgcatgtgt ccgatggca ccctgtttaa agtgcaggtc  900
accagccaga atatgggatg tcagattagc gataacccctt gtgggaatac tcattaa     957

SEQ ID NO: 3           moltype = AA   length = 318
FEATURE                Location/Qualifiers
source                 1..318
                       mol_type = protein
                       organism = Homo sapiens
SEQUENCE: 3
MAAAAAAAE QQSSNGPVKK SMREKAVERR SVNKEHNSNF KAGYIPIDED RLHKTGLRGR     60
KGNLAICVII LLFILAVINL IITLVIWAVI RIGPNGCDSM EFHESGLLRF KQVSDMGVIH  120
PLYKSTVGGR RNENLVITGN NQPIVFQQGT TKLSVENNKT SITSDIGMQF FDPRTQNILF  180
STDYETHEFH LPSGVKSLNV QKASTERITS NATSDLNIKV DGRAIVRGNE GVFIMGKTIE  240
FHMGGNMELK AENSIILNGS VMVSTTRLPS SSSGDQLGSG DWVRYKLCMC ADGTLFKVQV  300
TSQNMGCQIS DNPCGNTH                                                318

SEQ ID NO: 4           moltype = DNA   length = 148
FEATURE                Location/Qualifiers
misc_feature           1..148
                       note = 5' chimeric intron sequence
source                 1..148
                       mol_type = other DNA
                       organism = synthetic construct
SEQUENCE: 4
gggtacaatt ccgcagcttt tagagcagaa gtaacacttc cgtacaggcc tagaagtaaa   60
ggcaacatcc actgaggagc agttctttga tttgcaccac caccggatcc gggacctgaa  120
ataaaagaca aaaagactaa acttacct                                     148

SEQ ID NO: 5           moltype = DNA   length = 792
FEATURE                Location/Qualifiers
misc_feature           1..792
                       note = 5' MHCK7 promoter sequence
source                 1..792
                       mol_type = other DNA
                       organism = synthetic construct
SEQUENCE: 5
gctggctgct cctgagtgtc tgtctgtgct gtggaggtgg tggtagaatg agggcagccc   60
ctgtgccct gggttatata gaggagccta caggtgtga ctagccagga ggggctgtcc   120
ccagggaggg gcccctgaga gcagatgagc tttcagctcg ttgcccggc accgtgccca  180
ccccgaccc aggcgtgcag cttgcccagc cccatgcct tgtatgggc gccccaggg    240
ctgacttgct cactggttcc taaactaagt gctgagtcta gctggcgggg gacagctggc  300
ccttcgccgg gaacatggaa cagtaatact ttgggagtcc caggcacgta taagcctgg   360
cccccaagcc tgttacagcc tgccctcagt ccccacagc cttgttcgaa gatcttgca   420
tgcaggggat ccaccaggga cagggttatt tttagaggca gcaggtgttg ggggggggg   480
ggcagccaca tgtctgggtt aattataacc aggcatctcg tgtcccca ggccttgcct  540
ccttacatgg gcagcctaga cccgtagtgg ggcatgctag acagcagggc ccaaggtttt  600
gcccatgaaa ggtctgttgc cctcgcccct tggctccat ggcctttttt tagtccttgg  660
gcacattcct cctccccaaa gggccgatgg gcagatagag gagagacagg agcgtctcac  720
accacctccc ctacccaggc ccttacctca gttattttta atctgaaggg tctagcttag  780
acatgcaagc tt                                                      792

SEQ ID NO: 6           moltype = DNA   length = 52
FEATURE                Location/Qualifiers
misc_feature           1..52
                       note = 5' polyadenylation sequence
```

```
source                   1..52
                         mol_type = other DNA
                         organism = synthetic construct
SEQUENCE: 6
acaaaaaacc aacacacaga tctaatgaaa ataaagatct tttattgcgg cc              52

SEQ ID NO: 7             moltype = DNA  length = 125
FEATURE                  Location/Qualifiers
misc_feature             1..125
                         note = 5' ITR
source                   1..125
                         mol_type = other DNA
                         organism = synthetic construct
SEQUENCE: 7
aaccccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gggtt                                                                125

SEQ ID NO: 8             moltype = DNA  length = 130
FEATURE                  Location/Qualifiers
misc_feature             1..130
                         note = 3' ITR 1
source                   1..130
                         mol_type = other DNA
                         organism = synthetic construct
SEQUENCE: 8
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
agggggttcct                                                          130

SEQ ID NO: 9             moltype = DNA  length = 720
FEATURE                  Location/Qualifiers
misc_feature             1..720
                         note = tMCK
source                   1..720
                         mol_type = other DNA
                         organism = synthetic construct
SEQUENCE: 9
ccactacggg tctaggctgc ccatgtaagg aggcaaggcc tggggacacc cgagatgcct      60
ggttataatt aaccccaaca cctgctgccc cccccccccc aacacctgct gcctgagcct    120
gagcggttac cccaccccgg tgcctgggtc ttaggtctg tacaccatgg aggagaagct     180
cgctctaaaa ataaccctgt ccctggtgga tccactacgg gtctaggctg cccatgtaag    240
gaggcaaggc ctggggacac ccgagatgcc tggttataat taaccccaac acctgctgcc    300
cccccccccc caacacctgc tgcctgagcc tgagcggtta ccccaccccg gtgcctgggt    360
cttaggctct gtacaccatg gaggagaagc tcgctctaaa ataaccctgt ccctggtgg     420
atccactacg ggtctaggct gcccatgtaa ggaggcaagg cctggggaca cccgagatgc    480
ctggttataa ttaaccccaa cacctgctgc cccccccccc caacacctgc tgcctgagc     540
ctgagcggtt accccacccc ggtgcctggg tcttaggctc tgtacaccat ggaggagaag    600
ctcgctctaa aaataaccct gtccctggtg gatcctcccct ggggacagcc cctcctggct   660
agtcacaccc tgtaggctcc tctatataac caggggcac aggggctgcc cccgggtcac     720

SEQ ID NO: 10            moltype = DNA  length = 43
FEATURE                  Location/Qualifiers
misc_feature             1..43
                         note = Hairpin
source                   1..43
                         mol_type = other DNA
                         organism = synthetic construct
SEQUENCE: 10
cgcccgggca aagcccgggc gtcgggcgac ctttggtcgc ccg                       43

SEQ ID NO: 11            moltype = DNA  length = 957
FEATURE                  Location/Qualifiers
misc_feature             1..957
                         note = 5' hSGCB DNA
source                   1..957
                         mol_type = other DNA
                         organism = synthetic construct
SEQUENCE: 11
ttaatgagta tcccacaag ggttatcgct aatctgacat cccatattct ggctggtgac      60
ctgcacttta acagggtgc catcggcaca catgcacagc ttatacctga cccaatctcc    120
ggaccccagc tggtctccac tagaggagct gggcagtctg gtagtggaga ccatcacgct    180
cccattcaga atgatgctgt tttctgcttt cagctccatg ttgcctccca tgtgaaattc    240
aattgtcttg cccatgatga acacgccctc atttccccgg acaatagctc gtccatccac    300
cttgatattc aggtctgatg tagcgttact ggtgattctc tcagtgctgg ctttctggac    360
gttcagagac ttcaccccgg aaggcagatg aaattcgtgt gtctcatagt cggtactgaa    420
caggatattc tgggtccggg gatcaaagaa ctgcatgcca atgtcgctag tgattgatgt    480
tttattgttt tccacagaca gctttgtggt tccctgctgg aacacaatgg gctgattgtt    540
cccggtgatc accagattct cgtttctccg cccgccgaca gtagatttgt acagtggatg    600
```

```
gatgacccccc atatcggaca cctgcttaaa tcgcagcagg ccactttcgt ggaactccat    660
agagtcacac  ccgtttgggc caatgcggat gacagcccaa atcaccagag taatgatcag    720
attaatcacg  gccaggataa acagcagaat gatgacgcag attgccaggt ttcctttgcg    780
cccccctcagg cctgtcttat gcaggcgatc ttcgtcaata gggatgtagc cggctttgaa    840
attgctgttg  tgctccttat tcactgatct cctctcgacg gcttttttctc tcattgattt    900
tttcactggt  ccattgcttg actgctgctc ggcggctgcg gcggctgctg ctgccat       957

SEQ ID NO: 12          moltype = DNA   length = 148
FEATURE                Location/Qualifiers
misc_feature           1..148
                       note = 3' chimeric intron sequence Intron
source                 1..148
                       mol_type = other DNA
                       organism = synthetic construct
SEQUENCE: 12
aggtaagttt agtcttttttg tcttttattt caggtcccgg atccggtggt ggtgcaaatc     60
aaagaactgc tcctcagtgg atgttgcctt tacttctagg cctgtacgga agtgttactt    120
ctgctctaaa agctgcggaa ttgtaccc                                       148

SEQ ID NO: 13          moltype = DNA   length = 792
FEATURE                Location/Qualifiers
misc_feature           1..792
                       note = 3' MHCK7 promoter sequence MHCK7
source                 1..792
                       mol_type = other DNA
                       organism = synthetic construct
SEQUENCE: 13
aagcttgcat gtctaagcta gacccttcag attaaaaata actgaggtaa gggcctgggt     60
aggggaggtg gtgtgagacg ctcctgtctc tcctctatct gcccatcggc cctttgggga    120
ggaggaatgt gcccaaggac taaaaaaagg ccatggacgc agagggggca gggcaacaga    180
cctttcatgg gcaaaccttg gggccctgct gtctagcatg ccccactacg ggtctaggct    240
gcccatgtaa ggaggcaagg cctgggggaca cccgagatgc ctggttataa ttaacccaga    300
catgtggctg cccccccccc cccaacacct gctgcctcta aaaataaccc tgtccctggt    360
ggatcccctg catgcgaaga tcttcgaaca aggctgtggg ggactgaggg caggctgtaa    420
caggcttggg ggcagggct tatacgtgcc tgggactccc aaagtattac tgttccatgt    480
tcccggcgaa gggccagctg tccccgcca gctagactca gcacttagtt taggaaccag    540
tgagcaagtc agcccttggg gcagcccata caaggccatg gggctgggca agctgcacgc    600
ctgggtccgg ggtgggcacg gtgcccgggc aacgagctga aagctcatct gctctcaggg    660
gccccctccct ggggacagcc cctcctggct agtcacaccc tgtaggctcc tctatataac    720
ccaggggcac aggggctgcc ctcattctac caccacctcc acagcacaga cagacactca    780
ggagcagcca gc                                                        792

SEQ ID NO: 14          moltype = DNA   length = 54
FEATURE                Location/Qualifiers
misc_feature           1..54
                       note = 3' polyadenylation sequence PolyA
source                 1..54
                       mol_type = other DNA
                       organism = synthetic construct
SEQUENCE: 14
ggccgcaata aaagatcttt attttcatta gatctgtgtg ttggttttttt gtgt          54

SEQ ID NO: 15          moltype = DNA   length = 130
FEATURE                Location/Qualifiers
misc_feature           1..130
                       note = 3' ITR 2
source                 1..130
                       mol_type = other DNA
                       organism = synthetic construct
SEQUENCE: 15
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag                                                           130
```

SELF-COMPLEMENTARY ADENO-ASSOCIATED VIRUS VECTOR AND ITS USE IN TREATMENT OF MUSCULAR DYSTROPHY

This application claims priority benefit of U.S. Provisional Application No. 63/256,368, filed Oct. 15, 2021, which is incorporated by reference herein in its entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 56758_Seqlisting.txt; Size: 28,732 bytes; Created: Sep. 28, 2022.

FIELD OF THE INVENTION

Described herein are therapy vectors such as AAV vectors expressing β-sarcoglycan and method of using these vectors to reduce and prevent fibrosis in subjects suffering from a muscular dystrophy.

BACKGROUND

LGMDs are rare conditions and they present differently in different people with respect to age of onset, areas of muscle weakness, heart and respiratory involvement, rate of progression and severity. LGMDs can begin in childhood, adolescence, young adulthood or even later. Both genders are affected equally. LGMDs cause weakness in the shoulder and pelvic girdle, with nearby muscles in the upper legs and arms sometimes also weakening with time. Weakness of the legs often appears before that of the arms. Facial muscles are usually unaffected. As the condition progresses, people can have problems with walking and may need to use a wheelchair over time. The involvement of shoulder and arm muscles can lead to difficulty in raising arms over head and in lifting objects. In some types of LGMD, the heart and breathing muscles may be involved.

There are at least nineteen forms of LGMD, and the forms are classified by their associated genetic defects.

| Type | Pattern of Inheritance | Gene or Chromosome |
| --- | --- | --- |
| LGMD1A | Autosomal dominant | Myotilin gene |
| LGMD1B | Autosomal dominant | Lamin A/C gene |
| LGMD1C | Autosomal dominant | Caveolin gene |
| LGMD1D | Autosomal dominant | Chromosome 7 |
| LGMD1E | Autosomal dominant | Desmin gene |
| LGMD1F | Autosomal dominant | Chromosome 7 |
| LGMD1G | Autosomal dominant | Chromosome 4 |
| LGMD2A | Autosomal recessive | Calpain-3 gene |
| LGMD2B | Autosomal recessive | Dysferlin gene |
| LGMD2C | Autosomal recessive | Gamma-sarcoglycan gene |
| LGMD2D | Autosomal recessive | Alpha-sarcoglycan gene |
| LGMD2E | Autosomal recessive | Beta-sarcoglycan gene |
| LGMD2F | Autosomal recessive | Delta-sarcoglycan gene |
| LGMD2G | Autosomal recessive | Telethonin gene |
| LGMD2H | Autosomal recessive | TRIM32 |
| LGMD2I | Autosomal recessive | FKRP gene |
| LGMD2J | Autosomal recessive | Titin gene |
| LGMD2K | Autosomal recessive | POMT1 gene |
| LGMD2L | Autosomal recessive | Fukutin gene |

Limb-girdle muscular dystrophy (LGMD) type 2E (LGMD2E) is an autosomal recessive disorder resulting from mutations in the gene encoding β-sarcoglycan (SGCB), causing loss of functional protein. LGMD2E represents a relatively common and severe form of LGMD in the United States with worldwide reports of incidence of 1/200,000-1/350,000 (Moore et al. J Neuropathol Exp Neurol 2006; 65: 995-1003). The absence of β-sarcoglycan leads to a progressive dystrophy with chronic muscle fiber loss, inflammation, fat replacement and fibrosis, all resulting in deteriorating muscle strength and function. (Araishi et al., Hum Mol Genet 1999; 8: 1589-1598, Durbee et al., Mol Cell 2000; 5: 141-151) As a complex, the sarcoglycans (α-, β, γ-, δ-), ranging in size between 35 and 50 kD, are all transmembrane proteins that provide stability to the sarcolemma offering protection from mechanical stress during muscle activity. (Araishi et al., Hum Mol Genet 1999; 8: 1589-1598) Loss of β-sarcoglycan in LGMD2E usually results in varying degrees of concomitant loss of other sarcoglycan proteins contributing to the fragility of the muscle membrane leading to loss of myofibers. 1 Although the range of clinical phenotype of LGMD2E varies, diagnosis typically occurs before age 10 and with loss of ambulation occurring by mid to late teens. Patients present with elevated serum creatine kinase (CK), proximal muscle weakness, difficulty arising from the floor and progressive loss of ambulation. Cardiac involvement occurs in as many as fifty percent of cases Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in see U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sci USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics.

An emerging form of therapy for LGMD2E is viral-mediated gene delivery to restore wild-type protein to affected muscle resulting in restoration of muscle function. Considering that a subset of patients can develop cardiomyopathy, (Fannin et al., Neuromusc Disord 2003; 13: 303-309, Sveen et al., Arch Neurol 2008; 65: 1196-1201, Melacini et al., Muscle Nerve 1999; 22: 473-479, Barresi et al., J Med Genet 2000; 37: 102-107) this would have to be considered in the long-term care of these patients. In previous reports, the Sgcb-null mouse was well characterized. Araishi et al. developed the β-sarcoglycan-deficient mouse with accompanying loss of all of the sarcoglycans as well as sarcospan, with at least minor preservation of merosin, the dystroglycans and dystrophin, reproducing the clinical picture seen in LGMD2E. The histological changes in this animal model were also a prototype for the clinical counterpart, including the prominence of skeletal muscle fibrosis. (Gibertini et al., Cell Tissue Res 2014; 356: 427-443) Dressman et al. (Dressman et al., Hum Gene Ther 2002; 13: 1631-1646) injected the transverse abdominal muscle using rAAV2.CMV.SGCB. Expression persisted for 21 months and muscle fibers were protected from recurrent necrosis. The use of self-complementary AAV to enhance transgene expression (McCarty et al., Gene Ther 2001; 8: 1248-1254), a muscle-specific promoter to better target skeletal muscle (Wang et al., Gene Ther 2008; 15: 1489-1499; Rodino-Klapac et al., Neurology 2008; 71: 240-247) and the optimization of a human β-sarcoglycan gene (hSGCB) has also been described.

Functional improvement in patients suffering from LGMD and other muscular dystrophies require both gene restoration and reduction of fibrosis. There is a need for methods of reducing fibrosis that may be paired with gene restoration methods for more effective treatments of LGMD and other muscular dystrophies.

SUMMARY

Described herein are gene therapy vectors, e.g. AAV, expressing the β-sarcoglycan gene and methods of delivering β-sarcoglycan to the muscle to reduce and/or prevent fibrosis; and/or to increase muscular force, and/or to treat a mammalian subject suffering from muscular dystrophy.

Provided herein are self-complementary AAV (scAAV) that express the β-sarcoglycan gene. For example, the provided scAAV comprise a polynucleotide sequence comprising i) two nucleotide sequence encoding the β-sarcoglycan protein which are self complementary, ii) two polyadenylation sequences which are self complementary and comprises a mutated inverted terminal repeat (ITR) located in center of the AAV genome sequence (expression cassette).

Also provided is a recombinant AAV (rAAV) vector comprising a polynucleotide sequence, wherein the polynucleotide sequence comprises, from 5' to the 3' direction, (1) a complementary sequence of a polyadenylation sequence; (2) a complementary sequence of a gene of interest; (3) a complementary sequence of an intron; (4) a complementary sequence of a promoter; (5) the 5' ITR sequence; (6) the promoter; (7) the intron; (8) the gene of interest; and (9) the polyadenylation sequence; wherein the polynucleotide sequence is flanked by two 3' ITR sequences, wherein the two 3' ITR sequences are complementary. In one embodiment, the gene of interest comprises human sarcoglycan-β(hSGCB), human sarcoglycan γ (hSGCG), human dysferlin, human ANO5, or calpain-3 (Cap 3) gene. In another embodiment, the promoter is a muscle specific control element. Examples of muscle specific control elements include human skeletal actin gene element, cardiac actin gene element, myocyte-specific enhancer binding factor MEF, muscle creatine kinase (MCK) promoter, MCK enhancer, truncated MCK (tMCK) promoter, tMCK enhancer, myosin heavy chain (MHC) promoter, MHCK7 promoter, C5-12 promoter, murine creatine kinase enhancer element, skeletal fast-twitch troponin c gene element, slow-twitch cardiac troponin c gene element, the slow-twitch troponin i gene element, hypoxia-inducible nuclear factor binding element, or steroid-inducible element or glucocorticoid response element (GRE).

Single strand AAV vectors (ssAAV), once in the nucleus, require cell-mediated synthesis of the second strand before it is ready for replication and transcription. However, the scAAV provided herein are superior to ssAAV in gene therapy because the scAAV bypasses the rate-limiting step of the cellular synthesis of the second-strand as required in a ssAAV.

Provided herein is a polynucleotide that comprises two self complementary nucleotide sequence (also referred to as expression cassettes), wherein in each nucleotide sequence comprises a MHCK7 promoter, a chimeric intron, the hSGCB cDNA sequence and a polyadenylation sequence and a single 5'ITR located in between the two nucleotide sequences. The 5' ITR creates a hairpin when the nucleotide sequences hybridize.

For example, the disclosure provides for the polynucleotide sequence of SEQ ID NO: 1, which is also set out as a schematic in FIG. 1. The polynucleotide sequence of SEQ ID NO: 1 is a 4511-nucleotide sequence which comprises two hSGCB cDNA sequences (SEQ ID NO: 2 and/or SEQ ID NO: 11), which encode the amino acid sequence of SEQ ID NO: 3 and hybridize to each other, two chimeric intron sequences (SEQ ID NO: 4 and/or SEQ ID NO: 11) which hybridize to each other, and two MHCK7 promoters (SEQ ID NO: 5 and/or SEQ ID NO: 13) which hybridize to each other and two polyadenyation sequences (SEQ ID NO: 6 and/or SEQ ID NO: 14) which hybridize to each other. An ITR sequence located in the center of the polynucleotide sequence has the nucleotide sequence set out as SEQ ID NO: 7. Additional ITR sequences are set out as SEQ ID NOS: 8 and 15.

The disclosure provides for a polynucleotide sequence comprising a nucleotide sequence at least about 90%, at least about 95% or at least about 99% identical to the nucleotide sequence of SEQ ID NO: 1. The disclosure also provide for a polynucleotide sequence comprising the nucleotide sequence of SEQ ID NO: 1.

In addition, the disclosure provides for recombinant AAV (rAAV) comprising any of the disclosed polynucleotides. For example, the disclosure provides for an rAAV comprising a polynucleotide sequence comprising the nucleotide sequence at least about 90%, at least about 95% or at least about 99% identical to the nucleotide sequence of SEQ ID NO: 1. The disclosure also provide an rAAV comprising a polynucleotide sequence comprising the nucleotide sequence of SEQ ID NO: 1.

The disclosure also provides for rAAV comprising the polynucleotide sequence wherein the polynucleotide sequence comprises i) two self complementary nucleotide sequences, each encoding a gene of interest, wherein the two self complementary nucleotide sequences encoding the gene of interest flank a 5' ITR sequence, ii) two self complementary polyadenylation sequences, wherein the polynucleotide sequence is flanked by two 3' ITR sequences, wherein the two 3' ITR sequences are complementary. For example, the gene of interest is GAD, MTM1, LPL, RPE, REP-1, CNGB3, P1ND4, XLRS, FVIII, FIX, FIX19, AAT, NF-KB, IFN-β, ARSA, NGF, hARSB, Neurturin, AADC, SUMF, SUMF1, OTC, FGF-4, ND4, ARSA, REP1, cytosine deaminase, HGF728, HGF723, hGAA, β-globin gene, Gag, MG1MA3, L523S, METRAP, GDNF, AQP1, PG9DP, HBB, ADA, TCR, CAR, Filgrastim, IL-12, GM-CSF, ICP34.5, PENK, RB94, SST2, DCK. P53, HSC, human sarcoglycan-β(hSGCB), human sarcoglycan Y (hSGCG), human dysferlin, human ANO5, calpain-3 (Cap 3) gene. For example, in the polynucleotide sequence the first nucleotide sequence is the complement sequence of the gene of interest and the second nucleotide sequence encoding the gene of interest is its sense sequence, so that the first nucleotide sequence and the second sequence nucleotide sequence are complementary to each other.

The recombinant AAV of claim 3, wherein the gene of interest is human sarcoglycan-β (hSCGB)(hSGCB), human sarcoglycan γ (hSCGG)(hSGCG), human dysferlin, human ANO5, or calpain-3 (Cap 3) gene.

The disclosure also provides for rAAV comprising a polynucleotide, wherein the polynucleotide sequence comprises i) two self complementary nucleotide sequences, each encoding the human β-sarcoglycan (hSGCB) protein, such as the amino acid sequence of SEQ ID NO: 3, ii) two self complementary polyadenylation sequences. In some embodiments, the nucleotide sequence encoding the hSGCB protein is at least about 90%, at least about 95% or at least about 99% identical to the nucleotide sequence of SEQ ID NO: 2, or the nucleotide sequence encoding the hSGCB protein comprises the nucleotide sequence of SEQ ID NO: 2. For example, the polyadenylated sequence comprises the nucleotide sequence of SEQ ID NO: 6.

In another aspect, described herein a recombinant AAV vector comprising a polynucleotide sequence encoding β-sarcoglycan. In some embodiments, the polynucleotide sequence encoding β-sarcoglycan comprises a sequence e.g. at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 5 or SEQ ID NO: 2 and encodes protein that retains β-sarcoglycan activity. In some embodiments, the polynucleotide sequence encoding β-sarcoglycan comprises the nucleotide sequence set forth in SEQ ID NO: 2. In some embodiments, the polynucleotide sequence encoding β-sarcoglycan consists of the nucleotide sequence set forth in SEQ ID NO: 5 or SEQ ID NO: 2.

In another aspect, a recombinant AAV vector described herein comprises a polynucleotide sequence encoding β-sarcoglycan that is at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the amino acid sequence of SEQ ID NO: 3, and the protein retains β-sarcoglycan activity.

In another aspect, described herein is a recombinant AAV vector comprising a polynucleotide sequence encoding functional β-sarcoglycan that comprises a nucleotide sequence that hybridizes under stringent conditions to the nucleic acid sequence of SEQ ID NO: 5 or SEQ ID NO: 2, or a complement thereof.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

When ranges are used herein for physical properties, such as molecular weight, concentration, or dosage, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England). Hybridization conditions can be adjusted by one skilled in the art in order to accommodate these variables and allow DNAs of different sequence relatedness to form hybrids.

In addition, any of the provided rAAV comprise a polynucleotide wherein each of the two self complementary nucleotide sequences is operably linked to a muscle-specific control element, wherein the two muscle-specific control elements are self complementary. For example, wherein the muscle-specific control element is human skeletal actin gene element, cardiac actin gene element, myocyte-specific enhancer binding factor (MEF), muscle creatine kinase (MCK) promoter, MCK element, truncated MCK (tMCK) promoter, tMCK element, myosin heavy chain (MHC) promter, MHCK7 promoter (a hybrid version of MHC and MCK), C5-12 promoter (synthetic promoter), murine creatine kinase enhancer element, skeletal fast-twitch troponin c gene element, slow-twitch cardiac troponin c gene element, the slow-twitch troponin i gene element, hypoxia-inducible nuclear factor binding element, steroid-inducible element or glucocorticoid response element (GRE).

In some embodiments, the disclosed rAAV comprises a polynucleotide sequence wherein each of the two complementary nucleotide sequence is operably linked to the muscle-specific control element MCK (tMCK) promoter comprising the nucleotide sequence of SEQ ID NO: 9. In other embodiments, the disclosed rAAV comprises a polynucleotide sequence wherein each of the two complementary nucleotide sequence is operably linked to the muscle-specific control element MHCK7 promoter comprising the nucleotide sequence of SEQ ID NO: 13 or SEQ ID NO: 5.

In further embodiments, the disclosed rAAV comprise a polynucleotide sequence comprising two complementary chimeric introns. For example, the chimeric intron comprises the nucleotide sequence of SEQ ID NO: 12 or SEQ ID NO: 4.

In addition embodiment, the disclosed rAAV comprise three inverted terminal repeats (ITRs), wherein one ITR is flanked by the two complementary muscle specific control elements. For example, the ITRs may comprise SEQ ID NO: 7 and/or SEQ ID NO: 8 and/or SEQ ID NO: 15. In a particular example, the ITR that is flanked by the two self-complementary muscle specific control elements comprise the nucleotide sequence of SEQ ID NO: 7. In other embodiments, two ITR's comprise the nucleotide sequence of SEQ ID NO:8 and SEQ ID NO: 15, and one of the ITR's comprises the nucleotide sequence of SEQ ID NO: 7.

The AAV can be any serotype, for example AAV1, AAV2, AAV3, AAV4, AAV5, AAV6, AAV7, AAV8, AAV9, AAV-10, AAV-11, AAV-12, AAV-13 and AAVrh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

The disclosure also provides for compositions comprising any of the disclosed rAAV or the disclosed polynucleotides. In some embodiments, the composition further comprises a pharmaceutically acceptable carrier, diluent and/or adjuvant. For example, the composition comprise any of the rAAV of the disclosure, a buffer agent, an ionic strength agent, and a surfactant.

In one aspect, described herein are methods of treating muscular dystrophy in a subject in need thereof comprising the step of administering to the subject any of the disclosed rAAV or any of the disclosed compositions.

In another aspect, the disclosure provides for methods of increasing muscular force and/or muscle mass in a subject suffering from muscular dystrophy comprising administering to the subject any of the disclosed rAAV or any of the disclosed compositions.

The disclosure also provides for methods of reducing contraction-induced injury in a subject suffering from muscular dystrophy comprising administering to the subject any of the disclosed rAAV or any of the disclosed compositions.

In addition, the disclosure provides for methods of treating β-sarcoglycanopathy in a subject comprising administering to the subject any of the disclosed rAAV or any of the disclosed compositions.

The disclosure also provided for methods of increasing beta-sarcoglycan positive fibers and/or decreasing CK level in a subject's muscle tissue comprising administering to the subject any of the disclosed rAAV or any of the disclosed compositions. For example, in any of the disclosed methods expression of the beta-sarcoglycan gene or the number of positive beta-sarcoglycan positive fibers is detected by measuring the beta-sarcoglycan protein level on a Western blot in muscle biopsies before and after administration of the rAAV. Alternatively, in any of the disclosed methods expression of beta-sarcoglycan gene or number of beta-sarcoglycan positive muscle fibers is detected by measuring the beta-sarcoglycan protein level by immunohistochemistry in muscle biopsies before and after administration of the rAAV.

In any of the disclosed methods, the subject is suffering from limb-girdle muscular dystrophy.

In any of the disclosed methods, the recombinant AAV or the composition is administered by intramuscular injection or intravenous injection. In other embodiments, the rAAV or the composition is administered systemically, such as administered intravenously.

In any of the disclosed methods, the recombinant AAV is administered at a dosage of $7.41 \times 10^{13}$ vg/kg measured by qPCR using linear reference plasmid or its equivalent dosage of $2 \times 10^{14}$ vg/kg measured by qPCR using supercoiled reference plasmid.

In another embodiment, in any of the disclosed methods, the recombinant AAV is administered at a dosage of $1.85 \times 10^{13}$ vg/kg measured by qPCR using linear reference plasmid or its equivalent dosage of $5 \times 10^{13}$ vg/kg measured by qPCR using supercoiled reference plasmid.

In one aspect, the disclosure provides for compositions for treating muscular dystrophy in a subject in need thereof, wherein the composition comprises any of the disclosed rAAV or any of the disclosed compositions.

In another aspect, the disclosure provides for compositions for increasing muscular force and/or muscle mass in a subject suffering from muscular dystrophy, wherein the composition comprises any of the disclosed rAAV or any of the disclosed compositions.

The disclosure also provides for compositions for reducing contraction-induced injury in a subject suffering from muscular dystrophy, wherein the composition comprises any of the disclosed rAAV or any of the disclosed compositions.

In addition, the disclosure provides for compositions for treating β-sarcoglycanopathy in a subject, wherein the composition comprises any of the disclosed rAAV or any of the disclosed compositions.

The disclosure also provided for compositions for increasing beta-sarcoglycan positive fibers and/or decreasing CK level in a subject's muscle tissue, wherein the composition comprises any of the disclosed rAAV or any of the disclosed compositions. For example, administration of the disclosed compositions results in an increase in expression of the beta-sarcoglycan gene or an increase in the number of positive beta-sarcoglycan positive fibers as detected by measuring the beta-sarcoglycan protein level on a Western blot in muscle biopsies before and after administration of the rAAV. Alternatively, administration of the disclosed compositions results in an increase in expression of beta-sarcoglycan gene or an increase in the number of beta-sarcoglycan positive muscle fibers as detected by measuring the beta-sarcoglycan protein level by immunohistochemistry in muscle biopsies before and after administration of the rAAV.

In any of the disclosed compositions, the subject is suffering from limb-girdle muscular dystrophy.

In any of the disclosed compositions, the recombinant AAV or the composition is formulated for administration by intramuscular injection or intravenous injection. In other embodiments, the rAAV or the composition is formulated for systemic administration, such as intravenous administration.

In any of the disclosed compositions, the recombinant AAV is at a dosage of $7.41 \times 10^{13}$ vg/kg measured by qPCR using linear reference plasmid or its equivalent dosage of $2 \times 10^{14}$ vg/kg measured by qPCR using supercoiled reference plasmid.

In another embodiment, in any of the disclosed compositions, the recombinant AAV is at a dosage of $1.85 \times 10^{13}$ vg/kg measured by qPCR using linear reference plasmid or its equivalent dosage of $5 \times 10^{13}$ vg/kg measured by qPCR using supercoiled reference plasmid.

In one aspect, described herein are uses of any of the disclosed rAAV or any of the disclosed compositions for preparation of a medicament for treating muscular dystrophy in a subject in need thereof.

In another aspect, the disclosure provides for uses of any of the disclosed rAAV or any of the disclosed compositions for preparation of a medicament for increasing muscular force and/or muscle mass in a mammalian subject suffering from muscular dystrophy.

The disclosure also provides for use of any of the disclosed rAAV or any of the disclosed compositions for preparation of a medicament for reducing contraction-induced injury in a subject suffering from muscular dystrophy.

In addition, the disclosure provides for uses of any of the disclosed rAAV or any of the disclosed compositions for preparation of a medicament for treating β-sarcoglycanopathy in a subject.

The disclosure also provided for use of any of the disclosed rAAV or any of the disclosed compositions for preparation of a medicament for increasing beta-sarcoglycan positive fibers and/or decreasing CK level in a subject's muscle tissue. For example, in any of the uses administration of the rAAV or the composition resulted in increased expression of the beta-sarcoglycan gene or the number of positive beta-sarcoglycan positive fibers as detected by measuring the beta-sarcoglycan protein level on a Western blot in muscle biopsies before and after administration of the rAAV. Alternatively, in any of the disclosed uses administration of the rAAV or composition results in increased expression of beta-sarcoglycan gene or number of beta-sarcoglycan positive muscle fibers as detected by measuring the beta-sarcoglycan protein level by immunohistochemistry in muscle biopsies before and after administration of the rAAV.

In any of the disclosed uses, the subject is suffering from limb-girdle muscular dystrophy.

In any of the disclosed uses, the recombinant AAV vector or the composition is formulated for administration by intramuscular injection or intravenous injection. In other embodiments, the rAAV or the composition is formulated for systemic administration, such as intravenous administration.

In any of the disclosed uses, the recombinant AAV is at a dosage of $7.41 \times 10^{13}$ vg/kg measured by qPCR using linear reference plasmid or its equivalent dosage of $2 \times 10^{14}$ vg/kg measured by qPCR using supercoiled reference plasmid.

In another embodiment, in any of the disclosed uses, the recombinant AAV is at a dosage of $1.85 \times 10^{13}$ vg/kg measured by qPCR using linear reference plasmid or its equivalent dosage of $5 \times 10^{13}$ vg/kg measured by qPCR using supercoiled reference plasmid.

In any of the disclosed methods, compositions or uses, the serum creatine kinase (CK) level in the subject is decreased after administration of the rAAV or the composition as compared to serum CK level before administration of the rAAV or the composition.

In another aspect, in any of the disclosed methods, compositions or uses, the level of beta-sarcoglycan gene expression in a cell of the subject is increased after administration of the rAAV or composition as compared to the level of beta-sarcoglycan gene expression before administration of the rAAV or composition; wherein the number of beta-sarcoglycan positive fibers in the muscle tissue of the subject is increased after administration of the rAAV as compared to the number of beta-sarcoglycan positive fibers before administration of the rAAV; or wherein motor function is improved in said subject as compared to the motor function of said subject before administration of the rAAV, and wherein the motor function is determined by a 100 meter timed walk test.

In one aspect, in any of the disclosed methods, compositions or uses the level of alpha-sarcoglycan gene expression is increased in a subject in need thereof after administration of the rAAV or composition as compared to the level of alpha-sarcoglycan gene expression before administration of the rAAV or composition. In another aspect, in any of the disclosed methods, composition or uses result in increased localization of alpha-sarcoglycan to a cell membrane in a subject in need thereof after administration of the rAAV or composition to the subject. In another aspect, in any of the disclosed methods, compositions or uses the level of alpha-sarcoglycan expression is increased in muscle tissue or the muscle function is improved in a subject in need thereof after administration of the rAAV as compared to the level of alpha-sarcoglycan expression or level of muscle function prior to administration the rAAV or composition.

In another aspect, the disclosure provides a method of increasing sarcoglycan expression in muscle tissue of a subject comprising administering to the subject any of the disclosed rAAV which encode hSGCB, and detecting increased expression of at least a second sarcoglycan in the cell membrane of the cell expressing said hSGCB. In some aspects, the second sarcoglycan is α-sarcoglycan (SGCA), γ-sarcoglycan (SGCG), or δ-sarcoglycan (SGCD).

In another aspect, provided is a method of generating the rAAV disclosed herein, comprising transferring a plasmid to a cell, wherein the plasmid comprises a nucleotide sequence that is at least about 90%, at least about 95%, or at least about 99% identical to SEQ ID NO: 1. In particular, the plasmid comprises a nucleotide sequence of SEQ ID NO: 1.

In any of the provided methods, compositions and uses, the level of beta-sarcoglycan gene expression in a cell of the subject is increased after administration of the rAAV or composition as compared to the level of beta-sarcoglycan gene expression before administration of the rAAV or composition; wherein the serum creatine kinase (CK) level in the subject is decreased after administration of the rAAV or the composition as compared to serum CK level before administration of the rAAV or composition; and/or wherein the number of beta-sarcoglycan positive fibers in the muscle tissue of the subject is increased after administration of the rAAV or composition as compared to the number of beta-sarcoglycan positive fibers before administration of the rAAV.

In another embodiment, in any of the provided methods, compositions and uses, motor function is improved in said subject as compared to the motor function of said subject before administration of the rAAV or composition, and wherein the motor function is determined by a 100 meter timed walk test. For example, motor function is improved by at least 5% in 1 month or thirty days post-gene transfer, at least 10% in 2 months or sixty days post-gene transfer, or at least 15% in 3 months or ninety days post gene transfer. In some embodiments, the motor function is improved by at least 5%, 10%, 15%, 20%, 25%, 30%, 40%, 45%, or 50%.

For example, in any of the provided methods, compositions and uses, the systemic route of administration is an intravenous route. For example, the rAAV is administered using an intravenous route and the dose of the rAAV administered is about $1.85 \times 10^{13}$ vg/kg or about $7.41 \times 10^{13}$ vg/kg based on a linearized plasmid as the quantification standard or the dose of the rAAV administered is about $5 \times 10^{13}$ vg/kg or about $2 \times 10^{14}$ vg/kg based on a supercoiled plasmid as the quantification standard.

In some embodiments, the dose of rAAV administered using an intravenous route and the dose is about $1.0 \times 10^{13}$ vg/kg to about $5 \times 10^{14}$ based on a supercoiled plasmid as the quantitation standard or about $1.0 \times 10^{13}$ vg/kg to about $1.0 \times 10^{14}$ vg/kg based on a linearized plasmid as the quantitation standard.

In addition, the dose of the rAAV administered is about $1.5 \times 10^{13}$ vg to about $2 \times 10^{16}$ vg, or $1.5 \times 10^{13}$ vg to $1 \times 10^{16}$ vg, or about $1.5 \times 10^{13}$ vg to about $2 \times 10^{15}$ vg, or about $1.5 \times 10^{13}$ vg to about $1 \times 10^{15}$ vg. In addition, in any of the methods, compositions and uses, the dose of rAAV is administered at a concentration of about 10 ml/kg. In any of the methods, compositions or uses provided, the muscular dystrophy is limb-girdle muscular dystrophy.

In any of the methods, uses and compositions for treating muscular dystrophy provided, the subject is 4-15 years of age, has confirmed beta-sarcoglycan (SGCB) mutation in both alleles, was negative for AAVrh74 antibodies and/or had >40% or normal 100 meter walk test. In any of the methods, uses and compositions of treating muscular dystrophy provided, the subject is a pediatric subject. In some embodiments, the subject is a pediatric subject, such as a subject ranging in age from 1 to 10 years. In some embodiments, the subject is 4 to 15 years of age. The subject, in one embodiment, is an adolescent subject, such as a subject ranging in age from 10 to 19 years. In addition, the subject, in one embodiment, is a young adult subject such as a subject ranging in age from late teens or early twenties, such as the subject may range in age from 15 to 29 years of age. In some embodiments, the subject is a middle-aged adult or an elderly subject, such that the middle-aged adult may range in age from 25-55 years of age and the elderly subject may range in age over 50 years of age.

In some embodiments, the rAAV is administered by injection, infusion or implantation. For example, the rAAV is administered by infusion over approximately 1 to 2 hours. In addition, the rAAV is administered by an intravenous route through a peripheral limb vein.

In any of the provided methods, uses or compositions, the subject suffers from a genetic mutation in a gene encoding a sarcoglycan or a muscular dystrophy. In some aspects, the sarcoglycan is β-sarcoglycan (SGCB), α-sarcoglycan (SGCA), γ-sarcoglycan (SGCG), or δ-sarcoglycan (SGCD). In some aspects, the sarcoglycan is β-sarcoglycan or α-sarcoglycan.

In any of the provided methods, uses or compositions, the level of beta-sarcoglycan protein is increased by at least 25%, or at least 26%, or at least 27%, or at least 28%, or at least 29%, or at least 30%, or at least 31%, or at least 32%, or at least 33%, or at least 34%, or at least or 35% or at least 36%, or at least 37%, or at least 38%, or at least 39%, or at least 40%, or at least 41%, or at least 42%, or at least 43%, or at least 44%, or at least 45% or at least 46%, or at least 47%, or at least 48%, or at least 49%, or at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 85%, or at least 90% or at least 95%, or at least 98% after administration of rAAV. For example, the level of the level of beta-sarcoglycan protein is increased by at least 33% as detected by measuring the beta-sarcoglycan protein level on a Western blot in muscle biopsied before and after administration of the rAAV, or the level of beta-sarcoglycan protein is increased by at least 38% or at least 39% as detected by measuring the beta-sarcoglycan protein level by immunohistochemistry in muscle biopsies before and after administration of the rAAV In any of the methods, uses or compositions provided herein, the serum CK level in the subject is decreased after administration of the rAAV as compared to serum CK level before administration of the rAAV. For example, the serum level CK level in the subject is decreased by at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 81%, or at least 82%, or at least 83%, or at least 84%, or at least 85%, or at least 86% or at least 87%, or at least 88%, or at least 89%, or at least 90% or at least 95%, or at least 98% by 60 to 90 days or 60 days or 90 days after administration of rAAV as compared to the serum CK level before administration of the rAAV.

In any of the methods, uses or compositions provided herein, the number of beta-sarcoglycan positive fibers in the muscle tissue of the subject is increased after administration of the rAAV as compared to the number of beta-sarcoglycan positive fibers before administration of the rAAV. For example, the number of beta-sarcoglycan positive fibers is detected by measuring the beta-sarcoglycan protein level by Western blot or immunohistochemistry on muscle biopsies before and after administration of the rAAV. For example, the number of beta-sarcoglycan positive fibers in the muscle tissue of the subject is increased by at least 25%, or at least 26%, or at least 27%, or at least 28%, or at least 29%, or at least 30%, or at least 31%, or at least 32%, or at least 33%, or at least 34%, or at least 35% or at least 36%, or at least 37%, or at least 38%, or at least 39%, or at least 40%, or at least 41%, or at least 42%, or at least 43%, or at least 44%, or at least 45% or at least 46%, or at least 47%, or at least 48%, or at least 49%, or at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 85%, or at least 90% or at least 95%, or at least 98% after administration of rAAV.

In any of the methods, compositions and uses provided herein, the level of alpha-sarcoglycan in the subject is increased after administration of the rAAV as compared to the level of alpha-sarcoglycan before administration of the rAAV. The level of alpha-sarcoglycan is detected by measuring the alpha-sarcoglycan protein level by immunohistochemistry or Western blot on muscle biopsies before and after administration of the rAAV.

In any of the provided methods, uses or compositions for expressing beta-sarcoglycan gene in a cell, expression of the beta-sarcoglycan gene in the cell is detected by measuring the beta-sarcoglycan protein level on a Western blot or immunohistochemistry in muscle biopsies before and after administration of any of the rAAV or compositions disclosed herein. For example, the cell has more than one AAV viral copy number. In addition, the beta-sarcoglycan gene is measured in the subject by detecting greater than 1 rAAV vector genome copy per nucleus.

In any of these methods, uses, and compositions, the serum CK level in the subject is decreased by at least 82% by 60 days after administration of any of the disclosed rAAV or compositions as compared to the serum CK level before administration of the rAAV.

In any of these methods, uses, and compositions, the number of beta-sarcoglycan positive fibers is detected by measuring the beta-sarcoglycan protein level by Western blot or immunohistochemistry on muscle biopsies before and after administration of the rAAV. In addition, in any of the methods, uses and compositions, the number of beta-sarcoglycan positive fibers is measured by detecting greater than 1 rAAV vector genome copy per nucleus.

In any of these methods, uses and compositions the level of alpha-sarcoglycan is detected by measuring the alpha-sarcoglycan protein level by Western blot or immunohistochemistry on muscle biopsies before and after administration of the rAAV. In addition, in any of the provided methods, uses and compositions, alpha-sarcoglycan is colocalized to the membrane of a cell expressing a beta-sarcoglycan encoded by scAAVrh74.MHCK7.hSGCB.

Methods of producing a recombinant AAV vector particle comprising culturing a cell that is transferred with a plasmid described herein and recovering recombinant AAV particles from the supernatant of the transfected cells are also provided. Viral particles comprising any of the recombinant AAV vectors described herein are also contemplated. In one embodiment, the method of generating the rAAV comprises transferring an AAV vector plasmid to a host cell. In another embodiment, the plasmid comprises a nucleotide sequence that is at least about 90%, at least about 95%, or at least about 99% identical to SEQ ID NO: 1. In another aspect, the disclosure provides a cell that comprising an AAV vector plasmid that comprises a nucleotide sequence of SEQ ID NO: 1. The cell described herein comprises may be an insect cell, e.g., a *Drosophila* cell (e.g., an S2 cell or Kc cell), a silkworm cell (e.g., a Bme21 cell), or a mosquito cell (e.g., a C6/36 cell); or a mammalian cell (preferably a human cell, e.g., a human primary cell or an established cell line). In one embodiment, the mammalian cell is a 293 cell, a COS cell, a HeLa cells, or a KB cell.

In another embodiment, the plasmid comprises a nucleotide sequence that is at least about 90%, at least about 95%, or at least about 99% identical to SEQ ID NO: 1. In some embodiments, the vector plasmid comprises a nucleotide sequence of any one of SEQ ID NO: 1. In some embodiments, the AAV vector plasmid is stably expressed in the host cell. The host cell stably harboring the AAV vector plasmid can be used to generate rAAV. In one embodiment, the AAV vector plasmid is a pAAV.MHCK7.hSGCB. KAN plasmid.

The method of producing recombinant AAV vector particles provided herein may further comprise a step of transferring a packaging plasmid and/or a helper virus to the host cell. For example, the methods further comprise a step wherein the packaging cell comprises a stably integrated AAV cap gene and/or wherein the packaging cell comprises a stably integrated AAV rep gene. The disclosure also provides for a cell comprising a plasmid that comprises a nucleotide sequence that is at least about 90%, at least about 95%, or at least about 99% identical to SEQ ID NO: 1 or a plasmid that comprises a nucleotide sequence of SEQ ID NO: 1. Also provided is a cell comprising a nucleotide sequence of SEQ ID NO: 1.

Methods of reducing fibrosis in a subject in need thereof is also provided. In this regard, the method comprises administering a therapeutically effective amount of an rAAV vector described herein (or composition comprising an rAAV vector described herein) to the mammalian subject. In some embodiments, the subject suffers from muscular dystrophy. In some embodiments, administration of an rAAV vector described herein (or composition comprising an rAAV vector described herein) reduces fibrosis in skeletal muscle or in cardiac muscle of the subject.

The term "muscular dystrophy" as used herein refers to a disorder in which strength and muscle bulk gradually decline. Non-limiting examples of muscular dystrophy diseases may include Becker muscular dystrophy, tibial muscular dystrophy, Duchenne muscular dystrophy, Emery-Dreifuss muscular dystrophy, facioscapulohumeral muscular dystrophy, sarcoglycanopathies, congenital muscular dystrophy such as congenital muscular dystrophy due to partial LAMA2 deficiency, merosin-deficient congenital muscular dystrophy, type 1D congenital muscular dystrophy, Fukuyama congenital muscular dystrophy, limb-girdle type 1A muscular dystrophy, limb-girdle type 2A muscular dystrophy, limb-girdle type 2B muscular dystrophy, limb-girdle type 2C muscular dystrophy, limb-girdle type 2D muscular dystrophy, limb-girdle type 2E muscular dystrophy, limb-girdle type 2F muscular dystrophy, limb-girdle type 2G muscular dystrophy, limb-girdle type 2H muscular dystrophy, limb-girdle type 21 muscular dystrophy, limb-girdle type 21 muscular dystrophy, limb-girdle type 2J muscular dystrophy, limb-girdle type 2K muscular dystrophy, limb-girdle type IC muscular dystrophy, rigid spine muscular dystrophy with epidermolysis bullosa simplex, oculopharyngeal muscular dystrophy, Ullrich congenital muscular dystrophy, and Ullrich scleroatonic muscular dystrophy. In some embodiments, the subject is suffering from limb-girdle muscular dystrophy. In some embodiments, the subject is suffering from limb-girdle muscular dystrophy type 2E (LGMD2E).

The term "fibrosis" as used herein refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include collagen, e.g. collagen 1, collagen 2 or collagen 3, and fibronectin.

In another aspect, described herein is a method of increasing muscular force and/or muscle mass in a mammalian subject comprising administering a therapeutically effective amount of an AAV vector described herein (or composition comprising an AAV vector described herein) to the mammalian subject. In one embodiment, the subject is a human.

In any of the provided formulations or compositions, the buffer agent comprises one or more of tris, tricine, Bistricine, HEPES, MOPS, TES, TAPS, PIPES, and CAPS. For example, the buffer agent comprises the tris with pH 8.0 at concentration of about 5 mM to about 40 mM or the buffer agent comprises the tris with pH 8.0 at about 20 mM.

In any of the provided formulations or compositions, the ionic strength agent comprises one or more of potassium chloride (KCl), potassium acetate, potassium sulfate, ammonium sulfate, ammonium chloride ($NH_4Cl$), ammonium acetate, magnesium chloride ($MgCl_2$), magnesium acetate, magnesium sulfate, manganese chloride ($MnCl_2$), manganese acetate, manganese sulfate, sodium chloride (NaCl), sodium acetate, lithium chloride (LiCl), and lithium acetate. For example, the ionic strength agent comprises $MgCl_2$ at a concentration of about 0.2 mM to about 4 mM or the ionic strength agent comprises NaCl at a concentration of about 50 mM to about 500 mM, or the ionic strength agent comprises $MgCl_2$ at a concentration of about 0.2 mM to about 4 mM and NaCl at a concentration of about 50 mM to about 500 mM, or the ionic strength agent comprises $MgCl_2$ at a concentration of about 1 mM and NaCl at a concentration of about 200 mM.

In any of the provided formulations or compositions, the surfactant comprises one or more of a sulfonate, a sulfate, a phosphonate, a phosphate, a Poloxamer, and a cationic surfactant. For example, the Poloxamer comprises one or more of Poloxamer 124, Poloxamer 181, Poloxamer 184, Poloxamer 188, Poloxamer 237, Poloxamer 331, Poloxamer 338, and Poloxamer 407. The Poloxamer may be at a concentration of about 0.00001% to about 1%. An exemplary surfactant is Poloxamer 188 at a concentration of about 0.001%.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

BRIEF DESCRIPTION OF THE FIGURES

FIG. 2A-2D provides an annotated nucleotide sequence of rAAVrh74.MHCK7.SGCB.

FIG. 7 demonstrates of rAAVrh74.MHCK7.SGCB (SRP-9003)-treated patients display an improvement in total NSAD score compared with natural history data.

DETAILED DESCRIPTION

Figure 1:
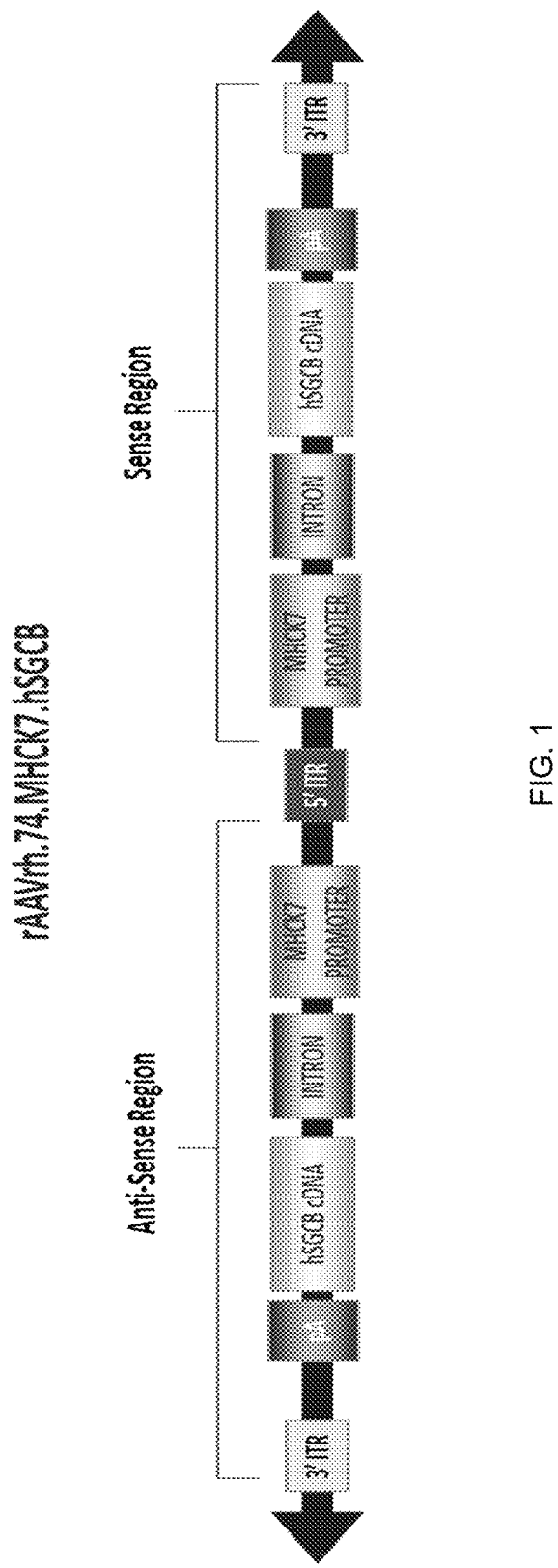
FIG. 1 provides a schematic of rAAVrh74.MHCK7.SGCB therapeutic β-sarcoglycan transgene cassette. Self-complementary AAV vector containing the codon-optimized human β-sarcoglycan gene (hSGCB). A muscle specific MHCK7 promoter drives expression. The cassette also contains a chimeric intron to augment processing and polyadenylation signal for stability.

The practice of the present invention will employ, unless otherwise indicated, conventional methods of virology, microbiology, molecular biology and recombinant DNA techniques within the skill of the art. Such techniques are explained fully in the literature. See, e.g., Sambrook et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijssen, ed.); Fundamental Virology, 2nd Edition, vol. I & II (B. N. Fields and D. M. Knipe, eds.); Freshney Culture of Animal Cells, A Manual of Basic Technique (Wiley-Liss, Third Edition); and Ausubel et al. (1991) Current Protocols in Molecular Biology (Wiley Interscience, N.Y.).

Definitions

As used herein, the singular forms "a," "an," and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. Reference to "a recombinant AAV" includes a mixture of two or more rAAV virions, and the like. All technical and scientific terms used herein have the same meaning as commonly understood to one of ordinary skill in the art to which this invention belongs unless clearly indicated otherwise.

The use of the term "or" in the claims is used to mean "and/or" unless explicitly indicated to refer to alternatives only, or the alternatives are mutually exclusive, although the disclosure supports a definition that refers to only alternatives and "and/or."

Throughout this application, the term "about" is used to indicate that a value includes the statistical experimental error (standard deviation of error) for the device or method being employed to determine the value.

The term "vector" is meant to be any genetic element, such as a plasmid, phage, transposon, cosmid, chromosome, virus, virion, etc., which is capable of replication when associated with the proper control elements and which can transfer gene sequences between cells. In one embodiment, the vector is a viral vector.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products. In one embodiment, the AAV vector is a vector derived from an adeno-associated virus serotype, including without limitation, AAV-1, AAV-2, AAV-3, AAV-4, AAV-5, AAV-6, AAV-7, AAV-8, AAV-9, AAV-10, AAV-11, AAV-12, AAV-13, AAV rh10, and AAVrh.74. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, as long as the sequences provide for functional rescue, replication and packaging.

The term "AAV helper functions" refer to AAV-derived coding sequences that can be expressed to provide AAV gene products that, in turn, function in trans for productive AAV replication. Thus, AAV helper functions comprise the major AAV open reading frames (ORFs), reps and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

By "recombinant virus" is meant a virus that has been genetically altered, e.g., by the addition or insertion of a heterologous nucleic acid sequence into the viral particle.

An "AAV virion" or "AAV viral particle" or "AAV vector particle" refers to a viral particle composed of at least one AAV capsid protein and an encapsidated polynucleotide AAV vector. The AAV virion, in one embodiment, comprises a heterologous polynucleotide (i.e. a polynucleotide other than a wild-type AAV genome such as a transgene to be delivered to a mammalian cell). Production of AAV viral particles, in some embodiments, includes production of AAV vector, as such a vector is contained within an AAV vector particle.

AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

For example, a wild-type (wt) AAV virus particle comprising a linear, single-stranded AAV nucleic acid genome associated with an AAV capsid protein coat. The AAV virion can be either a single-stranded (ss) AAV or self-complementary (SC) AAV. In one embodiment, a single-stranded AAV nucleic acid molecules of either complementary sense, e.g., "sense" or "antisense" strands, can be packaged into a AAV virion and both strands are equally infectious.

The term "recombinant AAV," or "rAAV" is defined herein as an infectious, replication-defective virus composed of an AAV protein shell, encapsidating a heterologous nucleotide sequence of interest which is flanked on both sides by AAV ITRs. An rAAV, in one embodiment, is produced in a suitable host cell which has an AAV vector, AAV helper functions and accessory functions introduced therein. In this manner, the host cell is capable of encoding AAV polypeptides that are required for packaging the AAV vector (containing a recombinant nucleotide sequence of interest) into infectious recombinant virion particles for subsequent gene delivery.

The term "transfection" refers to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a nucleotide integration vector and other nucleic acid molecules, into suitable host cells.

The term "host cell" denotes, for example, microorganisms, yeast cells, insect, cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The term "transduction" is used to refer to the administration/delivery of a polynucleotide of interest (e.g., a polynucleotide sequence encoding β-sarcoglycan) to a recipient cell either in vivo or in vitro, via a replication-deficient rAAV described resulting in expression of β-sarcoglycan by the recipient cell.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The nucleic acids include base analogues of DNA and RNA including, but not limited to 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil,-uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters." In one embodiment, the promoter is a muscle-specific promoter, which includes but is not limited to, a human skeletal actin gene element, a cardiac actin gene element, a desmin promoter, a skeletal alpha-actin (ASKA) promoter, a troponin I (TNNI2) promoter, a myocyte-specific enhancer binding factor mef binding element, a muscle creatine kinase (MCK) promoter, a truncated MCK (tMCK) promoter, a myosin heavy chain (MHC) promoter, a hybrid a-myosin heavy chain enhancer-/MCK enhancer-promoter (MHCK7) promoter, a C5-12 promoter, a murine creatine kinase enhancer element, a skeletal fast-twitch troponin c gene element, a slow-twitch cardiac troponin c gene element, a slow-twitch troponin i gene element, hypoxia-inducible nuclear factor (HIF)-response element (HRE), a steroid-inducible element, and a glucocorticoid response element (GRE). In another embodiment, the promoter is an MCK promoter, a tMCK promoter, or an MHCK7 promoter.

The term "operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A promoter "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA, at least one multiple cloning site, and a "mammalian" origin of replication (e.g., a SV40 or adenovirus origin of replication).

By "isolated" when referring to a nucleotide sequence, is meant that the indicated molecule is present in the substantial absence of other biological macromolecules such as other nucleotide sequences, chromatin material, etc. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3," or "5" relative to another sequence, it is to be understood that it is the position of the sequences in the "sense" or "coding" strand of a DNA molecule that is being referred to as is conventional in the art.

The terms "sequence identity", "percent sequence identity", or "percent identical" in the context of nucleic acid or amino acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. The percent identity of the sequences can be determined by techniques known in the art. For example, homology can be determined by a direct comparison of the sequence information between two polypeptide molecules by aligning the sequence information and using readily available computer programs such as ALIGN, ClustalW2 and BLAST. In one embodiment, when BLAST is used as the alignment tool, the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

The term "subject" refers to any member of the animal kingdom, which includes, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. In some embodiments, the subject is a human ranging in age from birth to 2 years, from 1 to 10 years, or ranging from 4 to 15 years, or ranging from 10 to 19 years, or from 20 to 40 years of age, or from 15 to 29 years of age or from 25-55 years, or ranging from 40 to 60 years, or over 50 years or over 60 years or over 65 years or over 70 years.

AAV

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., J Virol, 45: 555-564 (1983) as corrected by Ruffing et al., J Gen Virol, 75: 3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). Cloning of the AAVrh.74 serotype is described in Rodino-Klapac., et al. Journal of translational medicine 5, 45 (2007). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56oC to 65oC for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics.

Recombinant AAV genomes of the disclosure comprise nucleic acid molecule of the disclosure and one or more AAV ITRs flanking a nucleic acid molecule. AAV DNA in the rAAV genomes may be from any AAV serotype for which a recombinant virus can be derived including, but not limited to, AAV serotypes AAVrh.74, AAV-1, AAV-2, AAV-3, AAV-4, AAV-5, AAV-6, AAV-7, AAV-8, AAV-9, AAV-10, AAV-11, AAV-12, AAV-13, AAVrh. 10 and AAVrh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV serotypes are known in the art. To promote muscle-specific expression, AAVrh.74 can be used.

DNA plasmids of the disclosure comprise rAAV genomes of the disclosure. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAVrh.74, AAV-8, AAV-9, AAV-10, AAV-11, AAV-12, AAVrh. 10, AAVrh.74 and AAV-13. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); Mclaughlin et al., J. Virol., 62:1963 (1988); and Lebkowski et al., Mol. Cell. Biol., 7:349 (1988). Samulski et al., J. Virol., 63:3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. Vaccine 13:1244-1250 (1995); Paul et al. Human Gene Therapy 4:609-615 (1993); Clark et al. Gene Therapy 3:1124-1132 (1996); U.S. Pat. Nos. 5,786,211; 5,871,982; and 6,258,595. The foregoing documents are hereby incorporated by reference in their entirety herein, with particular emphasis on those sections of the documents relating to rAAV production.

The disclosure thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the disclosure comprise a rAAV genome. In exemplary embodiments, the genomes of both rAAV lack AAV rep and cap DNA, that is, there is no AAV rep or cap DNA between the ITRs of the genomes. Examples of rAAV that may be constructed to comprise the nucleic acid molecules of the disclosure are set out in International Patent Application No. PCT/US2012/047999 (WO 2013/016352) incorporated by reference herein in its entirety.

In an exemplary embodiment, the recombinant AAV vector of the disclosure is produced by the triple transfection method (Xiao et al., J Virol 72, 2224-2232 (1998) using the AAV vector plasmids scAAV.MHCK7.hSCGB, pNLRep2-Caprh74 and pHelp, rAAV contains the hSGCB gene expression cassette flanked by AAV2 inverted terminal repeat sequences (ITR). It is this sequence that is encapsidated into AAVrh.74 virions. The plasmid contains the hSGCB sequence and the MHCK7 enhancer and core promoter elements of the muscle specific promoter to drive gene expression. The expression cassette also contains an SV40 intron (SD/SA) to promote high-level gene expression and the bovine growth hormone polyadenylation signal is used for efficient transcription termination.

Figure 3:
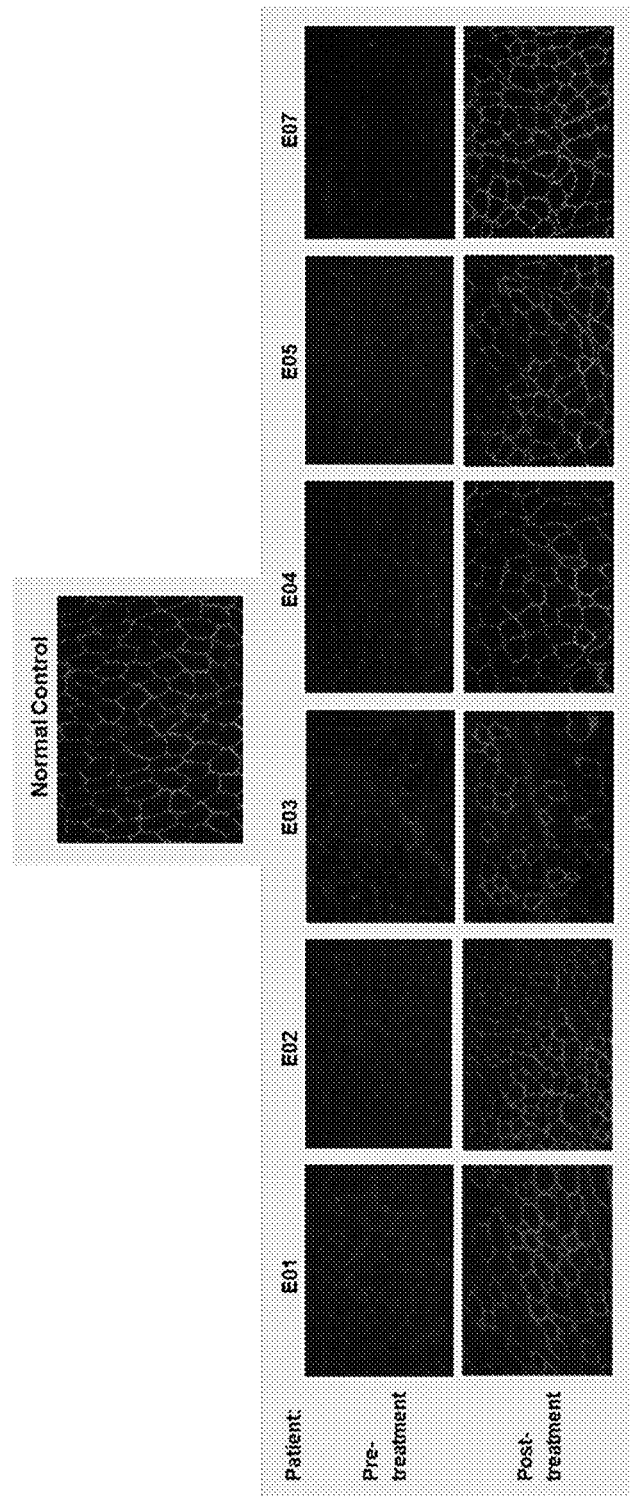
FIG. 3 demonstrates robust expression and sarcolemmal localization of SGCB at day 60 post-infusion of rAAVrh74.MHCK7.SGCB.

The pNLREP2-Caprh74 is an AAV helper plasmid that encodes the 4 wild-type AAV2 rep proteins and the 3 wild-type AAV VP capsid proteins from serotype rh74. A schematic map of the pNLREP2-Caprh74 plasmid is shown in FIG. 3.

Figure 4:
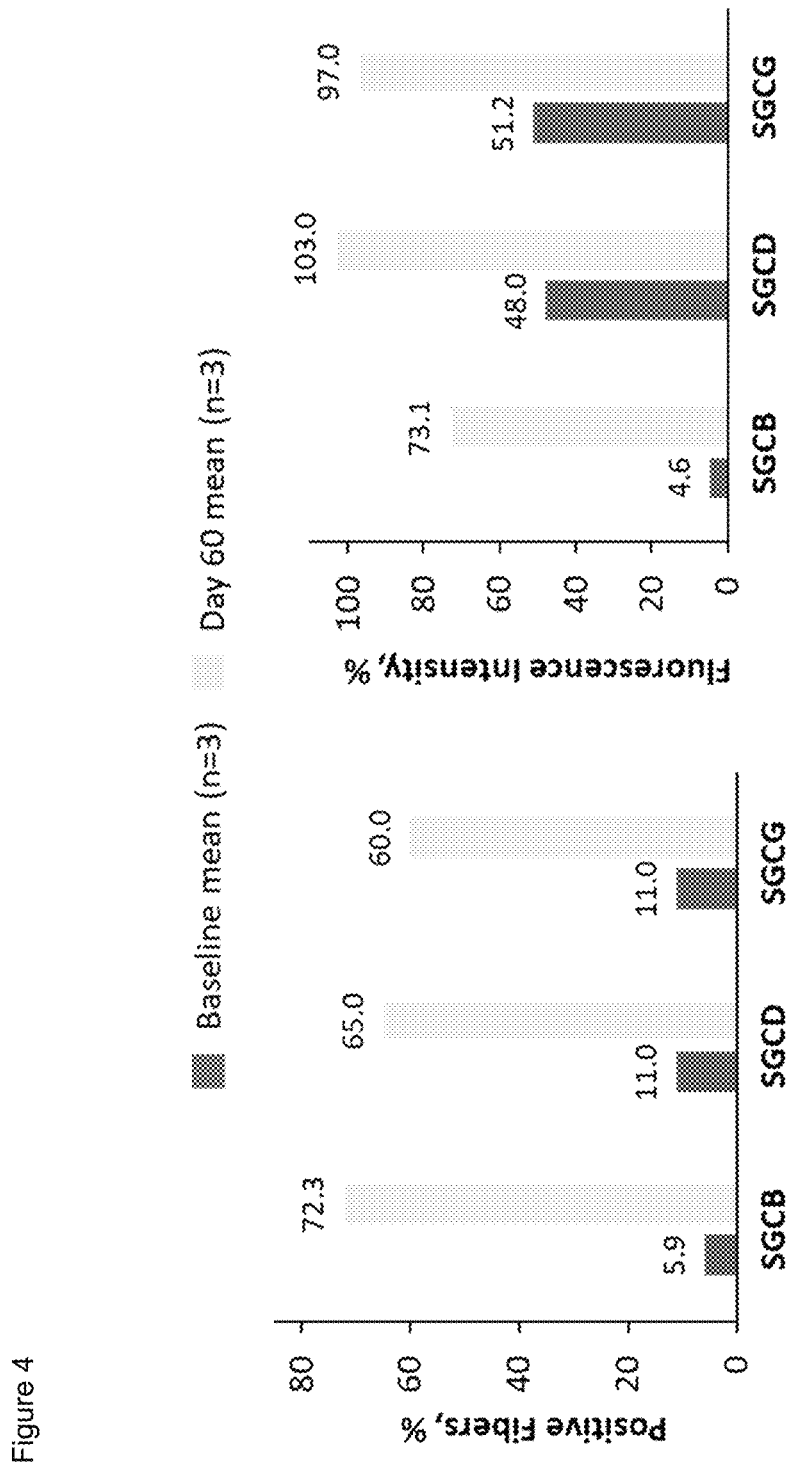
FIG. 4 demonstrates increased expression of SGCD and SGCG proteins at the sarcolemma at day 60 post-infusion of rAAVrh74.MHCK7.SGCB.

The pHELP adenovirus helper plasmid is 11,635 bp and was obtained from Applied Viromics. The plasmid contains the regions of adenovirus genome that are important for AAV replication, namely E2A, E4ORF6, and VA RNA (the adenovirus E1 functions are provided by the 293 cells). The adenovirus sequences present in this plasmid only represents ~40% of the adenovirus genome, and does not contain the cis elements critical for replication such as the adenovirus terminal repeats. Therefore, no infectious adenovirus is expected to be generated from such a production system. A schematic map of the pHELP plasmid is shown in FIG. 4.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the disclosure contemplates compositions comprising rAAV of the present disclosure. Compositions of the disclosure comprise rAAV and a pharmaceutically acceptable carrier. The compositions may also comprise other ingredients such as diluents and adjuvants. Acceptable carriers, diluents and adjuvants are nontoxic to recipients and are preferably inert at the dosages and concentrations employed and include buffers and surfactants such as pluronics.

Titers of rAAV to be administered in methods of the disclosure will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). One exemplary method of determining encapsilated vector genome titer uses quantitative PCR such as the methods described in (Pozsgai et al., Mol. Ther. 25(4): 855-869, 2017). Unless stated otherwise, the dosages described herein correspond to a dose as determined by the supercoiled DNA standard.

Methods of transducing a target cell with rAAV, in vivo or in vitro, are contemplated by the disclosure. The in vivo methods comprise the step of administering an effective dose, or effective multiple doses, of a composition comprising a rAAV of the disclosure to an animal (including a human being) in need thereof. If the dose is administered prior to development of a disorder/disease, the administration is prophylactic. If the dose is administered after the development of a disorder/disease, the administration is therapeutic. In embodiments of the disclosure, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the disclosure is muscular dystrophy, e.g. limb girdle muscular dystrophy or Duchenne muscular dystrophy.

Combination therapies are also contemplated by the disclosure. Combination as used herein includes both simultaneous treatment and sequential treatments. Combinations of methods of the disclosure with standard medical treatments (e.g., corticosteroids) are specifically contemplated, as are combinations with novel therapies.

Administration of an effective dose of the compositions, combination therapies or medicaments may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the disclosure may be chosen and/or matched by those skilled in the art taking into account the infection and/or disease state being treated and the target cells/tissue(s) that are to express the hSGCB protein.

The disclosure provides for local administration and systemic administration of an effective dose of rAAV, medicaments and compositions of the disclosure. For example, systemic administration is administration into the circulatory system so that the entire body is affected. Systemic administration includes enteral administration such as absorption through the gastrointestinal tract and parenteral administration through injection, infusion or implantation.

In particular, actual administration of rAAV of the present disclosure may be accomplished by using any physical method that will transport the rAAV recombinant vector into the target tissue of an animal. Administration according to the disclosure includes, but is not limited to, injection into muscle and injection into the bloodstream. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the disclosure. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the disclosure results in sustained expression of the hSGCB protein. The present disclosure thus provides methods of administering/delivering rAAV which express hSGCB protein to an animal, preferably a human being. These methods include transducing tissues (including, but not limited to, tissues such as muscle, organs such as liver and brain, and glands such as salivary glands) with one or more rAAV of the present disclosure. Transduction may be carried out with gene cassettes comprising tissue specific control elements. For example, one embodiment of the disclosure provides methods of transducing muscle cells and muscle tissues directed by muscle specific control elements, including, but not limited to, those derived from the actin and myosin gene families, such as from the myoD gene family (See Weintraub et al., Science, 251: 761-766 (1991)), the myocyte-specific enhancer binding factor MEF-2 (Cserjesi and Olson, Mol Cell Biol 11: 4854-4862 (1991)), control elements derived from the human skeletal actin gene (Muscat et al., Mol Cell Biol, 7: 4089-4099 (1987)), control elements derived from the cardiac actin gene, muscle creatine kinase sequence elements (See Johnson et al., Mol Cell Biol, 9:3393-3399 (1989)) and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factor binding element (Semenza et al., Proc Natl Acad Sci USA, 88: 5680-5684 (1991)), steroid-inducible elements and promoters including the glucocorticoid response element (GRE) (See Mader and White, Proc. Natl. Acad. Sci. USA 90: 5603-5607 (1993)), and other control elements.

Muscle tissue is an attractive target for in vivo DNA delivery, because it is not a vital organ and is easy to access. The disclosure contemplates sustained expression of hSGCB from transduced myofibers.

Thus, the disclosure provides methods of administering an effective dose (or doses, administered essentially simultaneously or doses given at intervals) of rAAV that encode hSGCB to a subject in need thereof.

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). The titers of rAAV may be determined by the supercoiled plasmid quantitation standard or the linearized plasmid quantitation standard.

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is muscular dystrophy, such as limb-girdle muscular dystrophy. Thus, provided is a method of transducing a target cell with an rAAV scAAVrh74.MHCK7.hSGCB, which comprises a nucleotide sequence of SEQ ID NO: 1.

Combination therapies are also contemplated by the invention. Combination as used herein includes both simultaneous treatment or sequential treatments. Combinations of methods of the invention with standard medical treatments (e.g., steroids, corticosteroids, and/or glucocorticoids including but not limited to one or more of prednisone, prednisolone; and deflazacort) are specifically contemplated, as are combinations with novel therapies. In this regard, the combinations include administering to a subject one or more steroids, corticosteroids, and/or glucocorticoids including but not limited to one or more of prednisone, prednisolone; and deflazacort before administering an rAAV of the inventive methods to the subject, simultaneously with administering the rAAV to the subject, or after administering the rAAV to the subject.

In related embodiments of a combination therapy contemplated by the invention, the glucocorticoid includes, but is not limited to beclomethasone, betamethasone, budesonide, cortisone, dexamethasone, hydrocortisone, methylprednisolone, or triamcinolone.

It is recognized that an antigen specific T-cell response may occur in a subject administered with the rAAV vector. This is an expected response between 2-4 weeks following gene transfer. One possible consequence to such antigen specific T-cell responses is clearance of the transduced cells and loss of transgene expression. To dampen the host immune response to the rAAV based therapy, before the therapy, for example, twenty-four hours prior to the therapy procedure, subjects can be started on approximately 1 mg/kg/day prophylactic prednisone or comparable glucocorticoid by mouth with a maximum dose of 60 mg/day. IV administration of a comparable glucocorticoid at the approximate dose of 1 mg/kg/day would also be allowable if needed. Treatment will continue for approximately one month. A tapering protocol for prednisone or comparable glucocorticoid can be implemented based on individual subjects' immune response to the gene transfer, assessed by ELISpot assay and also by liver function monitoring with GGT.

A therapeutically effective amount of the rAAV vector is a dose of rAAV ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg, 6e14 vg/kg, 7e14 vg/kg, 8e14 vg/kg, or 9e14 vg/kg. The invention also comprises compositions comprising these ranges of rAAV vector.

For example, a therapeutically effective amount of rAAV vector is a dose of 1e13 vg/kg, about 2e13 vg/kg, about 3e13 vg/kg, about 4e13 vg/kg, about 5e13 vg/kg, about 6e13 vg/kg, about 7e13 vg/kg, about 7.4e13 vg/kg, about 8e13 vg/kg, about 9e13 vg/kg, about 1e14 vg/kg, about 2e14 vg/kg, about 3e14 vg/kg, about 4e14 vg/kg and 5e14 vg/kg. The titer or dosage of AAV vectors can vary based on the physical forms of plasmid DNA as a quantitation standard. For example, the value of titer or dosage may vary based off of a supercoiled standard qPCR titering method or a linear standard qPCR tittering method. In one embodiment, a therapeutically effective amount of rAAV is a dose of 5e13 vg/kg based on a supercoiled plasmid as the quantitation standard or a dose of 1.85e13 vg/kg based on a linearized plasmid as the quantitation standard. In another embodiment, a therapeutically effective amount of rAAV is a dose of 2e14 vg/kg based on the supercoiled plasmid as the quantitation standard or a dose of 7.41e13 vg/kg based on the linearized plasmid as the quantitation standard. In another embodiment, the therapeutically effective amount of scAAVrh74.MHCK7.hSGCB is a dose ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg, 6e14 vg/kg, 7e14 vg/kg, 8e14 vg/kg, or 9e14 vg/kg, based on the supercoiled plasmid as the quantitation standard. The invention also comprises compositions comprising these doses of rAAV vector.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the β-sarcoglycan.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein.

Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling. Thus, in another aspect, the application is directed to a formulation that comprises an rAAV that comprises an AAVrh74 derived capsid, a buffer agent, an ionic strength agent, and a surfactant. In one embodiment, the rAAV is at a concentration of about $1.0 \times 10^{12}$ vg/ml to about $5.0 \times 10^{14}$ vg/ml. In another embodiment, the rAAV is at a concentration of about $5.0 \times 10^{12}$ vg/ml to about $1.0 \times 10^{14}$ vg/ml based on a supercoiled plasmid as the quantitation standard. In another embodiment, the rAAV is at a concentration of about $2.0 \times 10^{13}$ vg/ml based on a supercoiled plasmid as the quantitation standard. In one embodiment, the rAAV is an scAAVrh74.MHCK7.hSGCB vector. In one embodiment, the concentration of rAAV in the composition or formulation is from $1 \times 10^{13}$ vg/ml to $2 \times 10^{14}$ vg/ml based on a supercoiled plasmid as the quantitation standard. In another embodiment, the concentration is $2 \times 10^{13}$ vg/ml, $4 \times 10^{13}$ vg/ml, or $5 \times 10^{13}$ vg/ml based on a supercoiled plasmid as the quantitation standard. In one embodiment, the buffer agent comprises one or more of tris, tricine, Bis-tricine, HEPES, MOPS, TES, TAPS, PIPES, and CAPS. In another embodiment, the buffer agent comprises tris with pH 8.0 at concentration of about 5 mM to about 40 mM. In one embodiment, the buffer agent comprises tris with pH 8.0 at about 20 mM. In one embodiment, the ionic strength agent comprises one of more of potassium chloride (KCl), potassium acetate, potassium sulfate, ammonium sulfate, ammonium chloride ($NH_4Cl$), ammonium acetate, magnesium chloride ($MgCl_2$), magnesium acetate, magnesium sulfate, manganese chloride ($MnCl_2$), manganese acetate, manganese sulfate, sodium chloride (NaCl), sodium acetate, lithium chloride (LiCl), and lithium acetate. In one embodiment, the ionic strength agent comprises $MgCl_2$ at a concentration of about 0.2 mM to about 4 mM. In another embodiment, the ionic strength agent comprises NaCl at a concentration of about 50 mM to about 500 mM. In another embodiment, the ionic strength agent comprises $MgCl_2$ at a concentration of about 0.2 mM to about 4 mM and NaCl at a concentration of about 50 mM to about 500 mM. In another embodiment, the ionic strength agent comprises $MgCl_2$ at a concentration of about 1 mM and NaCl at a concentration of about 200 mM. In one embodiment, the surfactant comprises one or more of a sulfonate, a sulfate, a phosphonate, a phosphate, a Poloxamer, and a cationic surfactant. In one embodiment, the Poloxamer comprises one or more of Poloxamer 124, Poloxamer 181, Poloxamer 184, Poloxamer 188, Poloxamer 237, Poloxamer 331, Poloxamer 338, and Poloxamer 407. In one embodiment, the surfactant comprises the Poloxamer at a concentration of about 0.00001% to about 1%. In another embodiment, the surfactant comprises Poloxamer 188 at a concentration of about 0.001%. For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxpropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

Thus, also described herein are methods of administering an effective dose (or doses, administered essentially simultaneously or doses given at intervals) of rAAV that encode β-sarcoglycan to a mammalian subject in need thereof.

All publications and patents mentioned herein are hereby incorporated by reference in their entirety as if each individual publication or patent was specifically and individually indicated to be incorporated by reference. In case of conflict, the present application, including any definitions herein, will control.

The invention is further described in the following Examples, which do not limit the scope of the invention described in the claims.

EXAMPLES

Preclinical studies using scAAVrh74.MHCK7.hSGCB are described in International Patent Publication No. WO 2017/180976, which is incorporated by reference herein in its entirety.

Example 1 scAAVrh.74.MHCK7.hSGCB Construction

The transgene cassette containing a codon-optimized full-length human SGCB cDNA as shown in FIG. 1 was constructed. The cassette includes a consensus Kozak sequence (CCACC), an SV40 chimeric intron, a synthetic polyadenylation site, and the muscle-specific MHCK7 used to drive expression of the cassette. This is an MCK based promoter which utilizes a 206-bp enhancer taken from ~1.2 kb 5' of the transcription start site within the endogenous muscle creatine kinase gene with a proximal promoter (enh358MCK, 584-bp). The cassette was packaged into a self-complementary (sc) AAVrh.74 vector that is 93% homologous to AAV8. AAVrh.74 has been shown in mice and non-human primates to be safe and effective, particularly in crossing the vascular barrier when delivered to muscle through the circulation. (Chicoine et al., Mol Ther 2014; 22: 713-724., Rodino-Klapac et al., Mol Ther 2010; 18: 109-117, Chicoine et al., Mol Ther 2014; 22: 338-347)

A single strand AAV vector (ssAAV), once in the nucleus, requires cell-mediated synthesis of the second strand before it is ready for replication and transcription. An exemplary self-complementary AAV vector (scAAV) has the structure as set out in FIG. 1 and the annotated nucleotide sequence provided in FIG. 2 and is described in Table below. This scAAV is superior to ssAAV in gene therapy because the scAAV bypasses the rate-limiting step of the cellular synthesis of the second-strand as required in a ssAAV.

| Molecular Features of scAAVrh.74.MHCK7.hSGCB | | | | |
|---|---|---|---|---|
| TYPE | START | END | NAME | DESCRIPTION |
| REGION | 1 | 130 | 3' ITR | Self-complementary sequence 3' inverted terminal repeat |
| REGION | 27 | 69 | Hairpin | Hairpin within the 3' ITR |
| REGION | 204 | 255 | PolyA | Self-complementary sequence polyA |
| GENE | 262 | 1218 | hSCGB cDNA | Self-complementary hSCGB cDNA |
| REGION | 1228 | 1375 | Chimeric intron | 5' donor site from human β-globin gene and the branchpoint and 3' splice acceptor site from IgG heavy chain variable region |
| REGION | 1385 | 2176 | MHCK7 | Self-complementary mouse myosin heavy chain complex-E box muscle creatine kinase fusion enhancer/promoter |
| REGION | 2194 | 2318 | 5' ITR | 5' ITR |
| GENE | 2336 | 3127 | MHCK7 | Self-complementary mouse myosin heavy chain complex-E box muscle creatine kinase fusion enhancer/promoter |
| REGION | 3137 | 3284 | Chimeric intron | 5' donor site from human β-globin gene and the branchpoint and 3' splice acceptor site from IgG heavy chain variable region |
| GENE | 3294 | 4250 | hSCGB cDNA | hSCGB cDNA |
| REGION | 4257 | 4309 | PolyA | PolyA |
| REGION | 4382 | 4511 | 3' ITR | 3' ITR |

Example 2

LGMD2E Open-label Trial

Six patients treated with rAAVrh74.MHCK7.SGCB demonstrated robust target tissue transduction and transgene expression (biceps, TA) (FIG. 3), as well as clinical efficacy with improvement in multiple ambulatory clinical outcome measures. In this clinical dose-escalation study, two dose cohorts (each with n=3 patients) were evaluated where patients received rAAVrh74.MHCK7.SGCB (denoted to herein as "SRP-9003") at a dose of $1.85 \times 10^{13}$ vg/kg and $7.41 \times 10^{13}$ vg/kg via intravenous infusion. The dosage of $1.85 \times 10^{13}$ vg/kg was measured by qPCR using linear reference plasmid DNA qPCR with its supercoiled reference DNA equivalent at $5 \times 10^{13}$ vg/kg. The $7.41 \times 10^{13}$ vg/kg was measured by qPCR using linear reference plasmid DNA qPCR with its supercoiled reference DNA equivalent at $2 \times 10^{14}$ vg/kg.

As presented in Table 1, dose-dependent increase in both target tissue transduction (measured as vector genome copies per nucleus) and percent of β-SG protein (measured as immunofluorescence of mean percent β-sarcoglycan positive fibers (PBSGPF), and immunofluorescence of mean percent fluorescent expression (PFE), and total protein expression by Western Blot) was observed. Furthermore, in Cohort 1 patients treated with $1.84 \times 10^{13}$ vg/kg for whom the Year 2 biopsy has recently been obtained, the expression of β-SG was sustained at high levels between Day 60 and Year 2.

Table 1: Biological Activity of rAAVrh74.MHCK7.SGCB at Day 60 and Year 2 Post-Transfer as Measured by qPCR, Immunofluorescence, and Western Blot Methods

TABLE 1

Biological Activity of rAAVrh74.MHCK7.SGCB at Day 60 and Year 2 Post-Transfer as Measured by qPCR, Immunofluorescence, and Western Blot Methods

| Cohort | Cohort 1 ($1.85 \times 10^{13}$ vg/kg) | | | | Cohort 2 ($7.41 \times 10^{13}$ vg/kg) | | | |
|---|---|---|---|---|---|---|---|---|
| Patient No. | E01 | E02 | E03 | Mean | E04 | E05 | E07 | Mean |
| Day 60 gene expression assessments | | | | | | | | |
| Average vg copies/nucleus | 1.05 | 0.44 | 0.27 | 0.60 | 4.02 | 7.15 | 1.57 | 4.2 |
| Immunofluorescence: mean PβSGPF | 63% | 49% | 42% | 51% | 65% | 77% | 75% | 72% |
| Immunofluorescence: mean PFE | 47% | 57% | 38% | 47% | 55% | 67% | 97% | 73% |
| Western blot: % normal [a] | 35% | 39% | 35% | 36% | 53% | 63% | 70% | 62% |
| Year 2 gene expression assessments | | | | | | | | |
| Average vg copies/nucleus | 0.12 | 0.08 | 0.20 | 0.13 | — | — | — | — |
| Immunofluorescence: mean PβSGPF | 22% | 61% | 60% | 48% | — | — | — | — |
| Immunofluorescence: mean PFE | 9% | 51% | 46% | 35% | — | — | — | — |
| Western blot: % normal [a] | 37% | 69% | 56% | 54% | — | — | — | — |

PβSGPF = percent β-sarcoglycan positive fibers;
PFE = percent fluorescent expression;
qPCR = quantitative polymerase chain reaction;
vg = vector genome.
Data include tibialis anterior and biceps.
[a] Presented as percentage of normal. Normal control defined as the average wild-type β-sarcoglycan expression (n = 3).

A deficiency of beta-sarcoglycan (SGCB) protein leads to reduction or complete loss of the other sarcoglycan subunits from the membrane. Following administration of the SRP-9003, reconstitution of SGCB expression led to an increase in δ-sarcoglycan (SGCD) and γ-sarcoglycan (SGCG) expression (FIG. 4). The concomitant increases in expression of other sarcoglycans and localization of β-SG to the sarcolemmal membrane (as measured by percent SGCB positive fiber and fiber intensity) shows that the SGCB expression induced by rAAVrh74.MHCK7.SGCB was functional and localized correctly within the myocyte as would be expected for the native SGCB protein.

Figure 5:
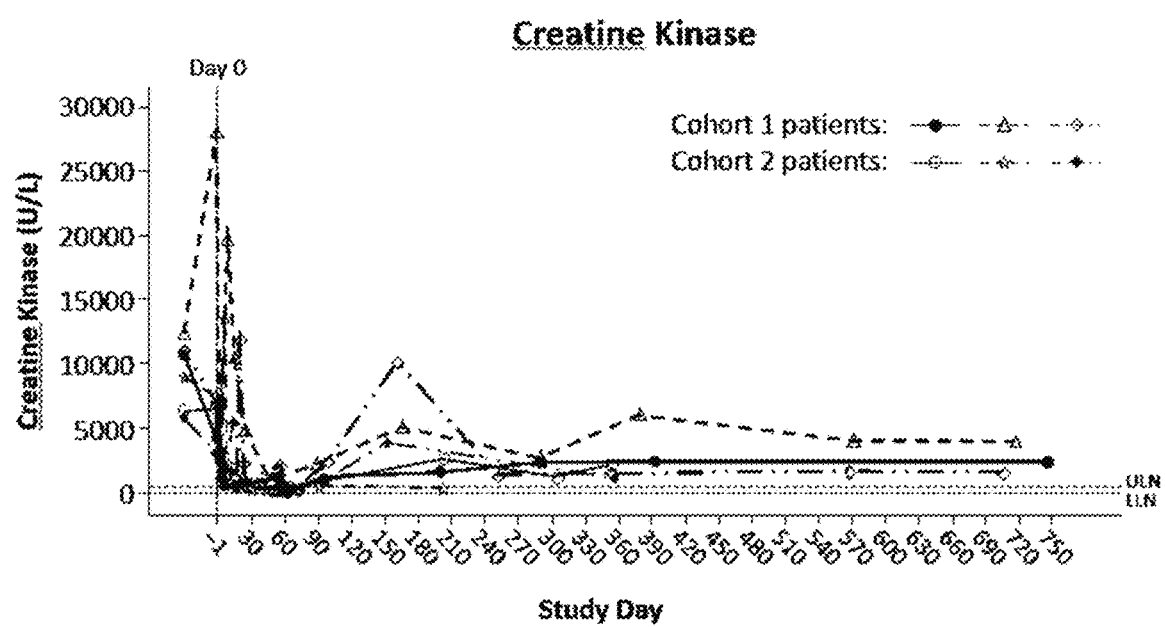
FIG. 5 demonstrates that reduction in creatine kinase (CK) after treatment with of rAAVrh74.MHCK7.SGCB (SRP-9003). LLN=lower limit of normal; ULN=upper limit of normal.

Elevated CK levels are inversely and statistically significantly correlated with disease duration (Semplicini 2015), implying that marked elevations in CK, such as those observed at Baseline in patients in Cohort 1, connote active processes of muscle deterioration (i.e., active disease prior to permanent deterioration). Systemic gene transfer with SRP-9003 led to early and deep reductions in mean CK levels, which were sustained (74%) at the day 750 assessments (FIG. 5).

Figure 6:
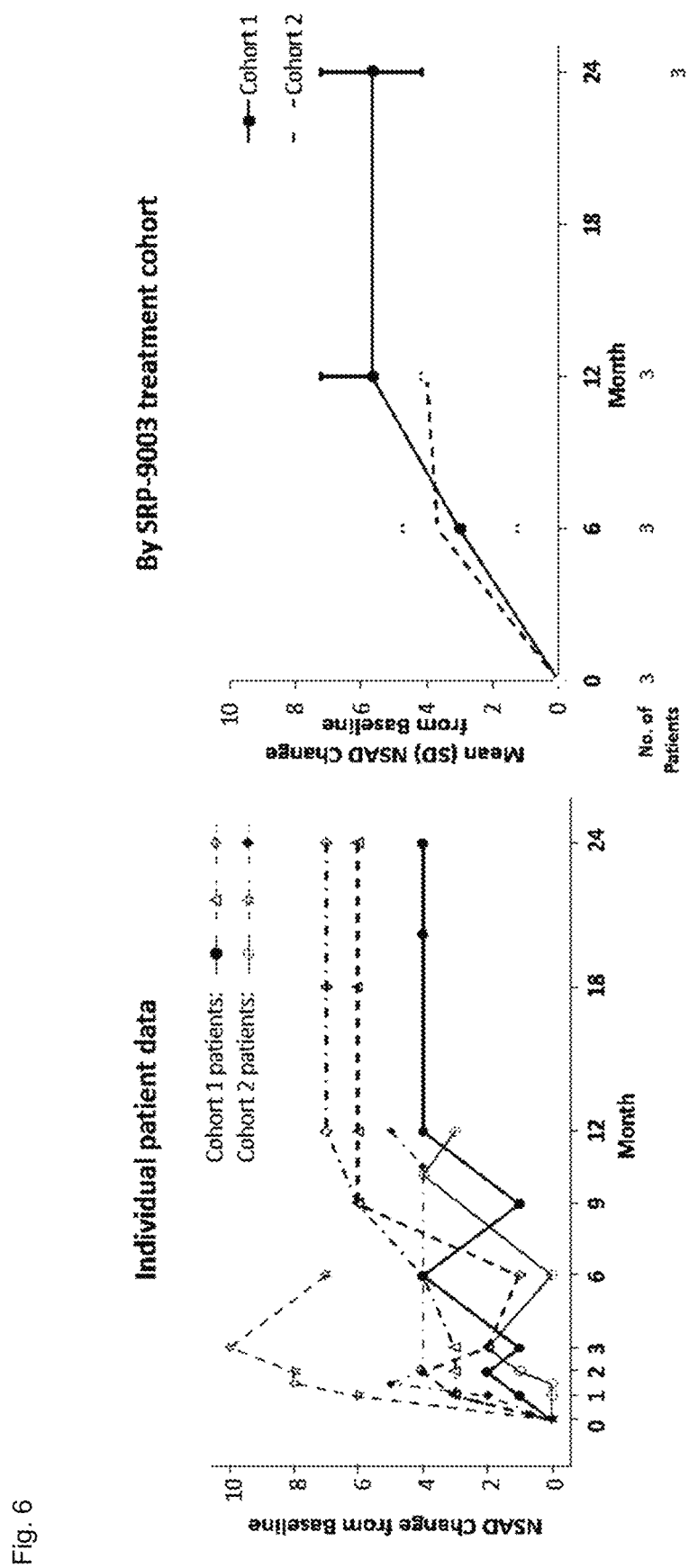
FIG. 6 demonstrates that of rAAVrh74.MHCK7.SGCB (SRP-9003) treatment results in sustained improvement in NSAD total score.

Patients who were treated with rAAVrh74.MHCK7.SGCB demonstrated clinically meaningful improvement in multiple functional motor assessments inclusive of North Star Assessment for Dysferlinopathy (NSAD) and timed function tests during Year 1 and Year 2 (FIG. 6 and Table 2). Functional improvements in both cohorts were most impressively noted by the overall 5 point improvements across the 2 dose cohorts in the total NSAD scores. Importantly, the improvements observed in the treated patients were sustained at the end of Year 2.

TABLE 2

Improvements over baseline in timed function tests

| Mean change from baseline (sec) | Cohort 1 (1.85 × 10$^{13}$ vg/kg) | | | Cohort 2 (7.41 × 10$^{13}$ vg/kg) | |
|---|---|---|---|---|---|
| | 6 months | 12 months | 24 months | 6 months | 12 months |
| Time to rise | −0.2 | −0.8 | −0.6 | −1.3 | −1.1 |
| 4-stair climb | −0.5 | −0.5 | −0.3 | −0.4 | −0.4 |
| 100 m | −3.8 | −5.3 | −2.8 | −6.3 | −7.9 |
| 10 m | −0.6 | −0.6 | −0.2 | −0.6 | −0.6 |

Example 3

Natural History Study

To select patients in the "natural history" control cohort for comparison with the treated patients in rAAVrh74.MHCK7.SGCB study, the following criteria, the same as the pre-defined inclusion criteria for the open label clinical study, were applied to the "natural history" dataset:
  Restricted to only LGMD2E/R4 ambulatory patients. For this cohort, it was defined as those with non-missing 10MWR value.
  Baseline age 4 through 15 years, inclusive
  100MWR test result: ≥40% of that predicted for age-, height-, gender-, and weight matched healthy controls With respect to the criteria applied to the overall "natural history" database in order to derive a natural history comparator for rAAVrh74.MHCK7.SGCB (SRP-9003) treated patients, from an overall dataset of 35 patients, 5 control patients who met these criteria were identified. The baselines between the treated cohort and natural history cohort are compared in Table 3. Age and gender are well balanced between rAAVrh74.MHCK7.SGCB treated subjects and "natural history" control cohort. Notably, baseline functional endpoints scores are higher in NCH control cohort.

TABLE 3

Baseline comparison of SRP-9003-treated patients with natural history cohort

| | SRP-9003-101 (N = 6) | NCH (N = 5) |
|---|---|---|
| Male, n (%) | 3 (50) | 3 (60) |
| Age (years) | 10.0 (3.5) | 9.8 (3.2) |
| NSAD | 41.2 (3.7) | 49.0 (3.9) |
| 100 m (sec) | 51.4 (10.5) | 38.9 (3.9) |
| 10 m (sec) | 5.1 (0.9) | 4.4 (0.3)$^a$ |

Following dosing of rAAVrh74.MHCK7.SGCB, an overall improvement was observed in the gene therapy treated subjects, compared to a downward trend in the "natural history" control cohort (FIG. 7). Individual subjects' change from baseline in NSAD scores are provided in NH=natural history; NSAD=North Star Assessment for Dysferlinopathy; SD=standard deviation. Patients treated with SRP-9003 demonstrated clinically meaningful improvements in functional outcomes in an exploratory comparison to an LGMD2E/R4 natural history cohort, as measured by NSAD.

The safety and tolerability of rAAVrh74.MHCK7.SGCB were determined by assessing adverse events, physical examinations, vital signs, serum and urine laboratory results, and immunogenicity at every visit through Month 18 for Cohort 1 and Month 6 for Cohort 2. In both cohorts, no other laboratory abnormalities were suggestive of safety concerns. No decreases in platelet counts were observed outside of the normal range. No clinical sequelae were associated with complement activation. Results show no new safety signals, and all treatment-related AEs occurred early and were transient and manageable.

REFERENCES

1 Bonnemann C G, Modi R, Noguchi S, Mizuno Y, Yoshida M, Gussoni E et al. Beta-sarcoglycan (A3b) mutations cause autosomal recessive muscular dystrophy with loss of the sarcoglycan complex. Nat Genet 1995; 11: 266-273.

2 Moore S A, Shilling C J, Westra S, Wall C, Wicklund M P, Stolle C et al. Limb-girdle muscular dystrophy in the United States. J Neuropathol Exp Neurol 2006; 65: 995-1003.

3 Araishi K, Sasaoka T, Imamura M, Noguchi S, Hama H, Wakabayashi E et al. Loss of the sarcoglycan complex and sarcospan leads to muscular dystrophy in beta-sarcoglycan-deficient mice. Hum Mol Genet 1999; 8: 1589-1598.

4 Durbeej M, Cohn R D, Hrstka R F, Moore S A, Allamand V, Davidson B L et al. Disruption of the beta-sarcoglycan gene reveals pathogenetic complexity of limb-girdle muscular dystrophy type 2E. Mol Cell 2000; 5: 141-151.

5 Bonnemann C G, Passos-Bueno M R, McNally E M, Vainzof M, de Sa Moreira E, Marie S K et al. Genomic screening for beta-sarcoglycan gene mutations: missense mutations may cause severe limb-girdle muscular dystrophy type 2E (LGMD 2E). Hum Mol Genet 1996; 5: 1953-1961.

6 Angelini C, Fanin M, Freda M P, Duggan D J, Siciliano G, Hoffman E P. The clinical spectrum of sarcoglycanopathies. Neurology 1999; 52: 176-179.

7 Sandona D, Betto R. Sarcoglycanopathies: molecular pathogenesis and therapeutic prospects. Exp Rev Mol Med 2009; 11: e28.
8 Fanin M, Melacini P, Boito C, Pegoraro E, Angelini C. LGMD2E patients risk developing dilated cardiomyopathy. Neuromusc Disord 2003; 13: 303-309.
9 Sveen M L, Thune J J, Kober L, Vissing J. Cardiac involvement in patients with limb-girdle muscular dystrophy type 2 and Becker muscular dystrophy. Arch Neurol 2008; 65: 1196-1201.
10 Melacini P, Fanin M, Duggan D J, Freda M P, Berardinelli A, Danieli G A et al. Heart involvement in muscular dystrophies due to sarcoglycan gene mutations. Muscle Nerve 1999; 22: 473-479.
11 Narayanaswami P, Weiss M, Selcen D, David W, Raynor E, Carter G et al. Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine. Neurology 2014; 83: 1453-1463.
12 Wong-Kisiel L C, Kuntz N L. Two siblings with limb-girdle muscular dystrophy type 2E responsive to deflazacort. Neuromusc Disord 2010; 20: 122-124.
13 Barresi R, Di Blasi C, Negri T, Brugnoni R, Vitali A, Felisari G et al. Disruption of heart sarcoglycan complex and severe cardiomyopathy caused by beta sarcoglycan mutations. J Med Genet 2000; 37: 102-107.
14 Gibertini S, Zanotti S, Savadori P, Curcio M, Saredi S, Salerno F et al. Fibrosis and inflammation are greater in muscles of beta-sarcoglycan-null mouse than mdx mouse. Cell Tissue Res 2014; 356: 427-443.
15 McCarty D M, Fu H, Monahan P E, Toulson C E, Naik P, Samulski R J. Adeno-associated virus terminal repeat (TR) mutant generates self-complementary vectors to overcome the rate-limiting step to transduction in vivo. Gene Ther 2003; 10: 2112-2118.
16 McCarty D M, Monahan P E, Samulski R J. Self-complementary recombinant adeno-associated virus (scAAV) vectors promote efficient transduction independently of DNA synthesis. Gene Ther 2001; 8: 1248-1254.
17 Chicoine L G, Rodino-Klapac L R, Shao G, Xu R, Bremer W G, Camboni M et al. Vascular delivery of rAAVrh74.MCK.GALGT2 to the gastrocnemius muscle of the rhesus macaque stimulates the expression of dystrophin and laminin alpha2 surrogates. Mol Ther 2014; 22: 713-724.
18 Rodino-Klapac L R, Montgomery C L, Bremer W G, Shontz K M, Malik V, Davis N et al. Persistent expression of FLAG-tagged micro dystrophin in nonhuman primates following intramuscular and vascular delivery. Mol Ther 2010; 18: 109-117.
19 Rodino-Klapac L R, Janssen P M, Montgomery C L, Coley B D, Chicoine L G, Clark K R et al. A translational approach for limb vascular delivery of the micro-dystrophin gene without high volume or high pressure for treatment of Duchenne muscular dystrophy. J Transl Med 2007; 5: 45.
20 Wang B, Li J, Fu F H, Chen C, Zhu X, Zhou L et al. Construction and analysis of compact muscle-specific promoters for AAV vectors. Gene Ther 2008; 15: 1489-1499.
21 Chicoine L G, Montgomery C L, Bremer W G, Shontz K M, Griffin D A, Heller K N et al. Plasmapheresis eliminates the negative impact of AAV antibodies on microdystrophin gene expression following vascular delivery. Mol Ther 2014; 22: 338-347.
22 Matsuda R, Nishikawa A, Tanaka H. Visualization of dystrophic muscle fibers in mdx mouse by vital staining with Evans blue: evidence of apoptosis in dystrophin-deficient muscle. J Biochem 1995; 118: 959-964.
23 Straub V, Rafael J A, Chamberlain J S, Campbell K P. Animal models for muscular dystrophy show different patterns of sarcolemmal disruption. J Cell Biol 1997; 139: 375-385.
24 Mendell J R, Sahenk Z, Malik V, Gomez A M, Flanigan K M, Lowes L P et al. A phase ½a follistatin gene therapy trial for becker muscular dystrophy. Mol Ther 2015; 23: 192-201.
25 Dressman D, Araishi K, Imamura M, Sasaoka T, Liu L A, Engvall E et al. Delivery of alpha- and beta-sarcoglycan by recombinant adeno-associated virus: efficient rescue of muscle, but differential toxicity. Hum Gene Ther 2002; 13: 1631-1646.
26 Rodino-Klapac L R, Lee J S, Mulligan R C, Clark K R, Mendell J R. Lack of toxicity of alpha-sarcoglycan overexpression supports clinical gene transfer trial in LGMD2D. Neurology 2008; 71: 240-247.
27 Shield M A, Haugen H S, Clegg C H, Hauschka S D. E-box sites and a proximal regulatory region of the muscle creatine kinase gene differentially regulate expression in diverse skeletal muscles and cardiac muscle of transgenic mice. Mol Cell Biol 1996; 16: 5058-5068.
28 Rabinowitz J E, Rolling F, Li C, Conrath H, Xiao W, Xiao X et al. Cross-packaging of a single adeno-associated virus (AAV) type 2 vector genome into multiple AAV serotypes enables transduction with broad specificity. J Virol 2002; 76: 791-801.
29 Grieger J C, Choi V W, Samulski R J. Production and characterization of adeno-associated viral vectors. Nat Protoc 2006; 1: 1412-1428.
30 Clark K R, Liu X, McGrath J P, Johnson P R. Highly purified recombinant adeno-associated virus vectors are biologically active and free of detectable helper and wild-type viruses. Hum Gene Ther 1999; 10: 1031-1039.
31 Liu M, Yue Y, Harper S Q, Grange R W, Chamberlain J S, Duan D. Adeno-associated virus-mediated microdystrophin expression protects young mdx muscle from contraction-induced injury. Mol Ther 2005; 11: 245-256.
32 Hakim C H, Grange R W, Duan D. The passive mechanical properties of the extensor digitorum longus muscle are compromised in 2- to 20-mo-old mdx mice. J Appl Physiol 2011; 110: 1656-1663.
33 Wein N, Vulin A, Falzarano M S, Szigyarto C A, Maiti B, Findlay A et al. Translation from a DMD exon 5 IRES results in a functional dystrophin isoform that attenuates dystrophinopathy in humans and mice. Nat Med 2014; 20: 992-1000.

What is claimed is:

1. A polynucleotide sequence comprising a first nucleotide sequence at least 95% identical to the nucleotide sequence of SEQ ID NO: 1, wherein SEQ ID NO: 1 comprises a second nucleotide sequence encoding a β-sarcoglycan protein.

2. The polynucleotide sequence of claim 1, wherein the first nucleotide sequence comprises the nucleotide sequence of SEQ ID NO: 1.

3. A composition comprising a recombinant AAV comprising the polynucleotide sequence of claim 1.

4. A method of treating muscular dystrophy in a subject in need thereof comprising administering to the subject a therapeutically effective amount of a recombinant AAV comprising the polynucleotide sequence of claim 1.

5. The method of claim 4, wherein the subject is suffering from limb-girdle muscular dystrophy.

6. The method of claim 4, wherein the recombinant AAV is administered systemically.

7. The method of claim 4, wherein the recombinant AAV is administered at i) a dosage of $7.41 \times 10^{13}$ vg/kg measured by qPCR using linear reference plasmid or its equivalent dosage of $2 \times 10^{14}$ vg/kg measured by qPCR using supercoiled reference plasmid or ii) a dosage of $1.85 \times 10^{13}$ vg/kg measured by qPCR using linear reference plasmid or its equivalent dosage of $5 \times 10^{13}$ vg/kg measured by qPCR using supercoiled reference plasmid.

8. The method of claim 7, wherein the recombinant AAV is administered intravenously.

9. A method of increasing muscle mass in a subject suffering from muscular dystrophy comprising administering to the subject a therapeutically effective amount of a recombinant AAV comprising the polynucleotide sequence of claim 1.

10. A method of treating β-sarcoglycanopathy in a subject comprising administering to the subject a therapeutically effective amount of a recombinant AAV comprising the polynucleotide sequence of claim 1.

11. A method of increasing beta-sarcoglycan positive fibers and/or decreasing CK levels in a subject's muscle tissue comprising administering to the subject a therapeutically effective amount of a recombinant AAV comprising the polynucleotide sequence of claim 1.

\* \* \* \* \*